US008822407B2

(12) United States Patent
Romagnani et al.

(10) Patent No.: US 8,822,407 B2
(45) Date of Patent: Sep. 2, 2014

(54) PREPARATION OF CONJUGATES COMPRISING ADENINE DERIVATIVES AND ALLERGENIC PROTEINS AND THEIR USE FOR SPECIFIC IMMUNOTHERAPY OF ALLENGENIC DISEASES

(75) Inventors: Sergio Romagnani, Florence (IT); Enrico Maggi, Florence (IT); Paola Parronchi, Florence (IT); Antonio Guarna, Seravezza (IT); Ernesto Giovanni Occhiato, Florence (IT)

(73) Assignee: Universita' Degli Studi di Firenze, Florence (IT)

( * ) Notice: Subject to any disclaimer, the term of this patent is extended or adjusted under 35 U.S.C. 154(b) by 0 days.

(21) Appl. No.: 13/814,370

(22) PCT Filed: Aug. 4, 2011

(86) PCT No.: PCT/IB2011/053482
§ 371 (c)(1),
(2), (4) Date: Feb. 5, 2013

(87) PCT Pub. No.: WO2012/017408
PCT Pub. Date: Feb. 9, 2012

(65) Prior Publication Data
US 2013/0136764 A1     May 30, 2013

(30) Foreign Application Priority Data
Aug. 5, 2010 (IT) .................... FI2010A0171

(51) Int. Cl.
*A61K 38/00* (2006.01)
(52) U.S. Cl.
USPC .......................................... 514/1.1
(58) Field of Classification Search
CPC ......... A61K 39/00; A61K 38/00; C07K 16/00
See application file for complete search history.

(56) References Cited
U.S. PATENT DOCUMENTS
7,754,728 B2 * 7/2010 Isobe et al. ............... 514/263.2

FOREIGN PATENT DOCUMENTS
EP    1035123 A1 *  9/2000
EP    1550662 A1    7/2005

OTHER PUBLICATIONS
Franssen et al., J. Med. Chem., 1992, 35, 1246-1259.*
Restani, et al., Allergy, 2004, 59 (Suppl. 78), 21-24.*
International Search Report for PCT/IB2011/053482 dated Dec. 1, 2011 (4 pages).

* cited by examiner

*Primary Examiner* — Marcela M Cordero Garcia
*Assistant Examiner* — Kaipeen Yang
(74) *Attorney, Agent, or Firm* — Abelman, Frayne & Schwab

(57) ABSTRACT

The present invention refers to the preparation of adenine derivative active esters of formula (I) and use thereof for the preparation of stable conjugates between adenine derivative and allergenic proteins having general structure (II) for the modulation of $T_H2$ response in allergic diseases. (I, II).

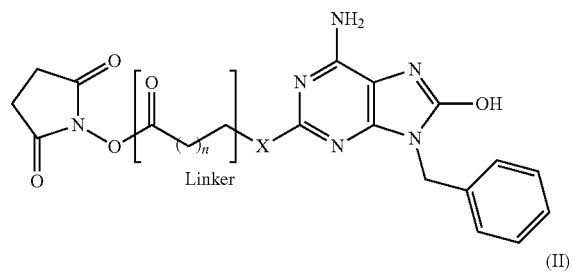

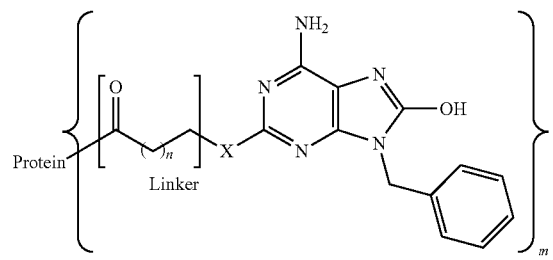

19 Claims, 11 Drawing Sheets p values: *<0.05,  <0.005, *<0.0005

PREPARATION OF CONJUGATES COMPRISING ADENINE DERIVATIVES AND ALLERGENIC PROTEINS AND THEIR USE FOR SPECIFIC IMMUNOTHERAPY OF ALLENGENIC DISEASES

RELATED APPLICATIONS

This application is a §371 of PCT/IB2011/053482 filed Aug. 4, 2011, and claims priority from Italian Patent Application No. FI2010A000171 filed Aug. 5, 2010, both incorporated by reference in their entirety.

FIELD OF THE INVENTION

The present invention falls within the field of vaccine preparation for specific immunotherapy.

STATE OF ART

At present several products for specific immunotherapy (SIT) are available on the market for the treatment of allergic diseases. However, SIT exhibits several limitations related to its profile of efficacy and safety. First of all, SIT is scarcely useful unless used in properly selected patients (selection based on the age, sensitizing allergen, entity of sensitization, etc). Secondly, SIT can determine an exaggerate release of mediators due to the stimulation of FceRI+ cells because of the administration of allergenic extracts to the patients with the possible consequence of severe adverse effects including anaphylactic shock. This implies that SIT cannot be used in those allergic diseases with more severe symptoms (bronchial asthma, atopic dermatitis, food allergy) in which the interference with allergen-specific response would be highly appreciable.

Antigen-specific immune response is mediated by two functionally distinct effector arms. While the T lymphocytes able to produce Interferon (IFN-)-gamma ($T_H 1$ lymphocytes) are responsible of protective responses against pathogens (intracellular bacteria, viruses), $T_H 2$ lymphocytes, able to produce IL-4, IL-5 and IL-13, are involved in the defence mechanisms towards parasites. A third subpopulation of lymphocytes, recently described as able to produce IL-17A (and, possibly, IL-22 and/or IFN-gamma) ($T_H 17$ lymphocytes) is responsible for the protective response against particular extracellular pathogens.

These three different cellular subpopulations are also responsible for several human diseases. In particular, allergic diseases (rhinitis, bronchial asthma, atopic dermatitis, food allergy, etc) are related to the expansion of $T_H 2$ cells specific for otherwise innocuous antigens (allergens) which are accumulated at the site of allergic inflammation (respiratory and/or gastro-intestinal tract, skin, etc). Even if several therapeutic options are available at the moment for the control of atopic diseases (steroids, anti-histamines, immunosuppressors), these drugs are only able to inhibit the activities of allergic mediators or, more generically and unspecifically, to regulate cellular activation.

Specific immunotherapy (SIT), used since the beginning of the last century, is intended to modify the allergy march and to prevent further sensitizations in atopic subjects but in the current practice it only partially meets these requirements. Actually, SIT should be based on the decrease of the activity of pathogenic $T_H 2$ cells together with a redirection of allergen-specific cells towards a more protective phenotype with production of IFN-gamma ($T_H 1$ cells). These activities might be possible by the use of novel and more powerful vaccine adjuvants which can induce the production of modulatory cytokines such as IFN-alfa and IL-12 through the interaction with particular Toll-like receptors (TLRs). Actually, some classes of low molecular weight compounds act as immunomodulatory agents both in vivo experimental animal models as well as on in vitro cultured human cells.

In particular, several evidences show that synthetic heterocycles chemically derived from adenine indeed exhibit immunomodulatory activities both in vivo and in vitro because of TLR7 activation with the induction of modulatory (IFN-alfa and others) and regulatory (IL-10) cytokines. At the same time these compounds reduce the production of $T_H 2$-related cytokines, inducing limited effects on B lymphocytes and low production of inflammatory cytokines. Finally, adenine derivatives have notable structural variability. The structural variability is strictly related to variable potencies in immunomodulation that is carried out at concentration usually ranging between 1 and 10 μM. These data suggest that these compounds may represent efficient and safe adjuvants to be used in vaccination protocols for the treatment of $T_H 2$-mediated diseases or, at least, in those pathologies where a protective IFN-gamma mediated immune response is hopeful.

However, even if the molecules that increase the vaccine potency through the stimulation of specific immune response and, possibly, redirect the immune response towards the wanted functional phenotype are the best adjuvants, it is also true that a simple combination (i.e. mixture) between an immunomodulator and proteins (from pathogens or exhibiting allergenic potential) affect several different cellular targets and, in particular, several antigen presenting cells. Thus, it would be necessary to use larger amounts of adjuvant to obtain the desired stimulatory effect with the possible amplification of adverse effects and reduction in the immune response specificity.

Thus, till now it is not yet solved how to direct an active adjuvant and an antigenic (or allergenic) protein at the same time to an unique antigen presenting cell in order to a) use lower amounts of adjuvant (with less toxic effects), b) act directly and exclusively on the antigen-specific response (reducing the release of inflammatory mediators), c) modulate the amount of adjuvant to the minimal active dose able to redirect the immune response.

EP1035123 describes 4-(-amino-9-benzyl-8-hydroxy-2-purinil)tiobutirric acid and its related methyl-ester. These two compounds are described together with other similar compounds and are claimed as useful as therapeutic agents in the immunologic diseases.

SUMMARY OF THE INVENTION

The present invention solves the above mentioned problems through stable conjugated compounds of formula (II) derived from the conjugation of a protein antigen and modified adenines via a covalent bond in which the formula (II) is the following

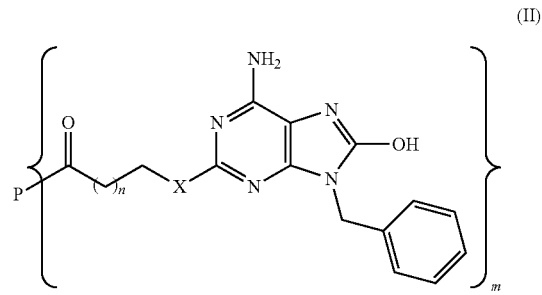

where X═S; n is a integer number between 0 and 18; P represents a protein antigen (highly purified or recombinant protein or semipurified extract) covalently bound to the modified adenines as an example (but non exclusively) through its lysine residues, where m is a integer number which can vary from m=1 to m=number of lysine residues present on the P protein.

It has been found that novel compounds of formula (II) derived from the conjugation of a protein antigen together with modified adenines are able to modify the allergen-specific response with re-direction towards a less pathogenic phenotype and, at the same time, exhibiting lower ability to stimulate the release of mediators of the allergic inflammation. This kind of redirecting response is determined by the synergistic activity of the antigen and the adenine derivative. This latter, as conjugated through a covalent bond, is active at significantly lower amounts than when used alone or simply mixed together with the antigen. This surprising synergy is possible because of the covalent conjugation between the protein of interest and the modified adenine. This result was also unexpected because of the great variability of chemical structures of adenine derivatives which exhibit different immunomodulatory activity as a) not all the structures (especially those with higher immunostimulatory activity) can be linked to protein antigens through covalent bonds, and b) it is not not trivial to covalently bind a protein to a modified adenine through a stable covalent bond.

Thus, subject-matter of the present invention are compounds with a chemical formula (II) described above for use as drugs (or as active ingredients in vaccine protocols and, in particular, in specific immunotherapy) for the treatment or, possibly, the prevention, of allergic diseases.

A further subject of the present invention are pharmaceutical compositions comprising at least one compound of formula (II) and at least another pharmaceutically acceptable ingredient. As pharmaceutical compositions vaccines are preferably considered.

A further object of the invention is a process for preparing compounds of formula (II), comprising the coupling of a protein P with an acid of formula (V), (V)

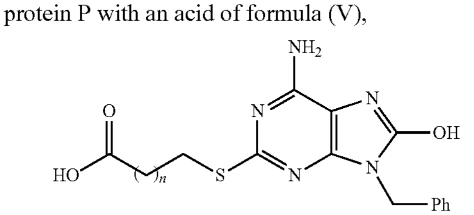

or a corresponding activated ester, where n is as defined above.

The conjugation is advantageously obtained by the use of activated esters from modified adenines of general structure (I)

(I)

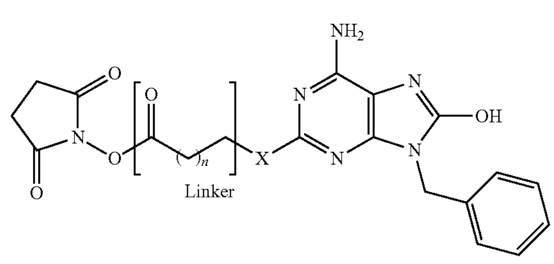

in which X═S and n represents the number of methylenic $CH_2$ units between 0 and 18. The molecular substructure $—CH_2—(CH_2)_n—CO$ will be defined as linker.

The compounds with general structure (I), as described above, are also subjects of the present invention. They have been demonstrated as able to efficiently react in mild conditions with allergenic proteins to produce stable conjugates with general structure (II).

Finally it is also a subject of the present invention a process for preparing compounds of formula (II) described above starting from compound of formula (III).

(III)

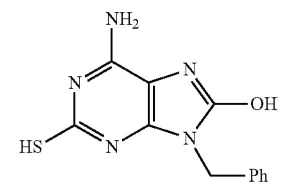

DETAILED DESCRIPTION OF THE INVENTION

In the structure (II) the antigen P can be represented by any of the protein antigens including, as examples, bacterial antigens, inhaled allergens as pollen allergens or animal dander derivatives or food allergens.

In some of the embodiments the antigen P has been selected among the following allergens: semipurified extract of the house dust mite *Dermatophagoides pteronyssinus* (DP), purified natural allergen Der p2 (major allergen from the house dust mite *Dermatophagoides pteronyssinus*) (nDer), recombinant allergen Der p2 (rDer) or ovalbumin (OVA grade V). In the compounds with formula (II) n is preferably included between 2 and 10, better n=2, 3, 4.

The novel compounds (II) derived from the conjugation of the above mentioned allergenic proteins together with modified adenines have been shown to exhibit immunomodulatory activity both in a in vitro system using human cells from atopic patients as well as an in vivo mouse models of allergy.

The results from the biological assays in which conjugates with structure (II) with n=2 and P one of the above mentioned proteins, obtained by the combination of allergenic proteins (both highly purified or recombinant proteins or semipurified extracts) and the active ester SA-26E (compound exhibiting formula (I) with n=2) are of absolute relevance and particular significance due to their immunomodulatory activities.

In particular, it has been found that:

the products obtained from the conjugation of the modified adenine named SA-26E together with the allergenic extract of the house dust mite *Dermatophagoides pteronyssinus* (both its natural purified form [nDer p2-conj] or semipurified form in which several allergenic proteins are contained [DP-conj]) stimulate the production of modulatory, regulatory and pro-inflammatory cytokines (IL-12p40, TNF-alfa, IL-6, IFN-alfa and IL-10) in highly purified monocytes and plasmacytoid dendritic cells from the peripheral blood of normal donors. This effect is similar to that obtained by the addition of already known soluble TLR ligands (lipopolysaccharide, CpG-ODN, R-848), whereas unconjugated allergens (nDer p2 and DP) are completely inactive. The soluble adenine SA-26E added at the same concentrations as present in nDer p2-conj is completely inactive.

The conjugated products nDer p2-conj and DP-conj induce NF-κB translocation into the nucleus as indicated by the increase of the nuclear expression of p50 in highly purified monocytes from the peripheral blood of normal subjects. Moreover, nDer p2-conj and DP-conj exclusively activate TLR7 in human or murine TLR-transfected HEK293. The unconjugated allergens nDer p2 and DP or the soluble SA-26E adenine (used at the same concentration as present in the nDer p2-conj conjugate) are completely inactive in the same experimental systems.

The conjugated products nDer p2-conj and DP-conj expand allergen-specific cells producing significantly lower amounts of IL-4, IL-5 and IL-13 with concomitant increase of IFN-gamma ($T_H0/T_H1$ cells instead of $T_H2$). The effect is confirmed at transcriptional level (decrease of GATA-3 and parallel increase of T-bet) and at clonal level. Finally, the conjugated products are also able to modify the functional phenotype of allergen-specific $T_H2$-established memory T cells (CRTH2 cells). No expansion of potentially pathogenic $T_H17$ cells has been observed. The soluble adenine SA-26E (used at the same concentration as present in the nDer p2-conj conjugate) is inactive in the same experimental conditions.

The conjugated products nDer p2-conj and DP-conj stimulate the proliferation of specific T cell blasts towards the unmodified allergens thus indicating that the conjugation procedure does not alter the integrity of the allergenic molecule.

The conjugated products nDer p2-conj and DP-conj induce a significantly lower rate of proliferation of highly purified B lymphocytes (which express high levels of TLR7) than other unconjugated TLR-ligands (R-848, CpG-ODN) or the soluble unconjugated modified adenine itself.

The conjugated products nDer p2-conj and DP-conj exhibit a significantly lower ability (than unmodified allergenic molecules) to activate circulating basophils from allergic donors. This indicates that conjugates exhibit lower ability to induce the mediator release from FcεRI+ cells. In addition, the conjugated allergen DP-conj is able to bind circulating IgE with a lower affinity than the unmodified allergen.

BALB/C and C57BL/6 mice sensitized by the use of an allergenic protein such as OVA or n Der p2 conjugated to the modified adenine have lower serum levels of both total and specific IgE (and significantly higher amounts of IgG2a) than mice sensitized with native OVA or nDer p2. Moreover, OVA-conj (or nDer p2-conj)-sensitized mice exhibit a significantly lower airway hyperreactivity than control animals.

It is possible to modulate the activity of conjugated products by varying the amount of the adenine bound to the allergenic protein thus obtaining a higher stimulatory activity on innate immune cells and a more profound redirecting effect towards a protective phenotype on allergen-specific cells.

The above specified data obtained with specific embodiments of the invention suggest that, on the basis of the general applicability of the conjugation procedure, similar results can be also obtained with other protein antigens.

According to the present invention, compounds of formula (II) can be obtained by reacting a compound having formula (V), as defined above, under conditions suitable to promote the amide bond formation between the linker carboxylic functionality and one or more lysine residues of the antigen P. To this end, it is possible to employ known conditions and catalysts for the formation of amide bonds; also, it is possible to transform the compound having formula (V) into a corresponding active ester. Among such active esters the compounds having formula (I) are to be preferred because they allow an efficient conjugation under mild conditions. Preferably, the conjugation reaction between a compound having formula (I) and an antigen P is carried out in a solution buffered at a pH between 7 and 8; more preferably at a pH between 7.2 and 7.6. Preferably, the solution is buffered with a phosphate buffer. Preferably, an excess of the active ester (I) is used compared to the moles of lysine evaluated to be present on the amount of the protein used; such an excess is preferably in the range of 1.5-8.0 equivalents. In the case of the conjugate in which n=2, P=nDer P2, the best biological results have been obtained with m=1, 2; higher substitutions (that is m values greater than 2) have produced an excessive cytolytic effect on the cells. Compound having formula (I) according to the invention in which X=S can be prepared from the adenine derivative (III) known from the literature. The derivative (III) can initially be (step a) functionalized with a linker by treatment with ROC(=O)—(CH$_2$)$_n$—Y, where Y is a leaving group such as Br, I, OTs, or OMs, R is a C1-C4 alkyl, n ranges from 0 to 18 (preferably between 2 and 10). To obtain a compound having formula (IV)

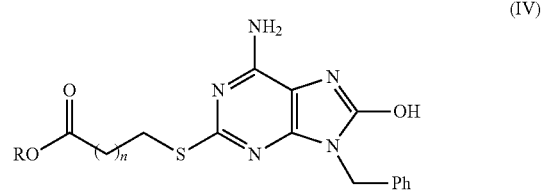

in which n and R are as above described.

Preferably Y is bromine and n=2, 3, 4.

Preferably in the step a about 1 equivalent of ROC(=O)—(CH$_2$)$_n$—Y is employed and preferably the reaction is carried in anhydrous DMF and in the presence of $K_2CO_3$ as a base.

The ester (IV) so obtained is hydrolyzed, preferably in alkaline medium with KOH in a 3:1 MeOH—$H_2O$ mixture, generating acid (V).

The active ester of formula (I) is prepared by treatment of acid (V) with a carbodiimide, preferably dicyclohexylcarbodiimide (in a slight excess), followed by N-hydroxysuccinimide under known conditions.

EXPERIMENTAL SECTION

Figure 1:
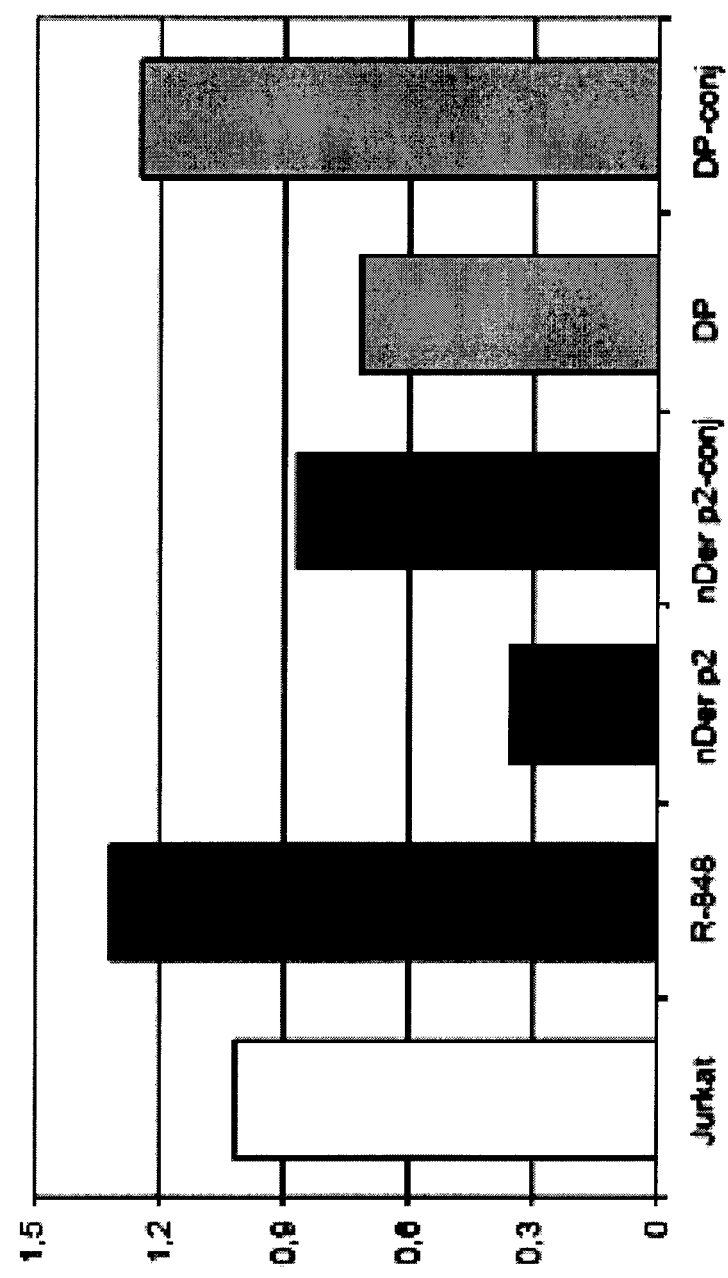
FIG. 1 shows the production of p50 due to NF-κB activation by purified CD14+ cells after the use of an already known TLR-ligand R-848, the allergenic proteins nDer p2 or DP extract and their respective conjugates nDer p2-conj (Conj-5) or DP-conj as specified in Example 4 (step a). As positive control the nuclear extract from Jurkat cells has been used according to the manufacturer's protocols. Levels of p50 (x-axis) are expressed as Optical Density. The figure shows a representative case.

The present invention can be better understood through the following examples.

The synthesis of the active ester of formula (II) has been realized starting from modified adenines already known from the literature. As an example of the preparation of an active ester with formula (I) the procedure for the active ester (SA-26E) in which X=S and n=2 is reported. All the other active esters with general formula (I) can be prepared using a similar methodology.

Example 1

Preparation of the Active Ester SA-26E

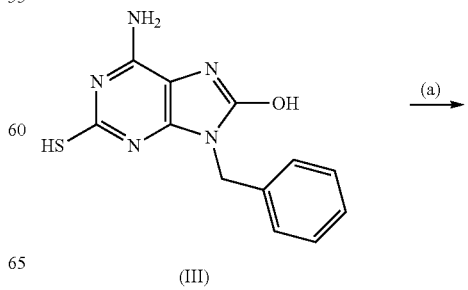

(III)

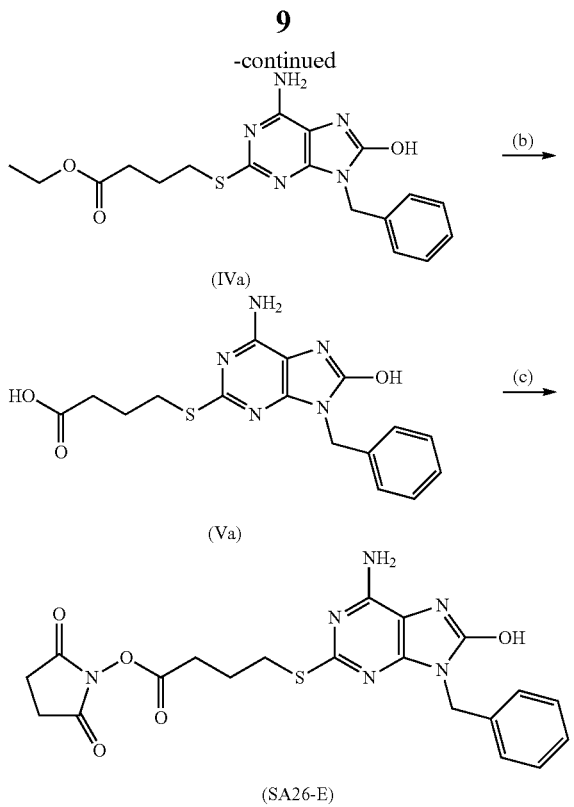

Adenine derivative (III) known from the literature has initially been functionalized with a linker by treatment with ethyl 4-bromobutanoate (1 equiv.) in anhydrous DMF and in the presence of $K_2CO_3$ as a base. The product (IVa) is thus obtained in 54% yield after chromatography. The ethyl ester (IVa) so obtained is hydrolyzed in alkaline medium with KOH in a 3:1 methanol-water mixture. After 48 h, the methanol is evaporated and the pH of the resulting solution is adjusted to pH 3 by 10% NaHSO4, thus leading to the precipitation of acid (Va) (70% yield). The active ester SA26-E is prepared by dissolving the acid (Va) in anhydrous DMF and adding dicyclohexylcarbodiimide in a slight excess followed by N-hydroxysuccinimide according to standard conditions. After chromatography of the crude reaction mixture the active ester SA26-E is obtained in a 79% yield.

Step (a)—Procedure for the preparation of 4-(6-Amino-9-benzyl-8-hydroxy-9H-purin-2-ylsulfanyl)-butyric Acid Ethyl Ester (IVa)

In a 100 mL two-necked flask, compound (III) (1.4 g, 5.12 mmol) is dissolved in 40 mL of anhydrous DMF under a nitrogen atmosphere. Molecular sieves (4 Å) are added in order to remove possible traces of water present in compound (III) and the solution is left under stirring at 25° C. for 35 min. $K_2CO_3$ (0.708 g, 5.12 mmol) is then added and the solution is left under stirring for 1 h. Ethyl 4-bromobutanoate (0.703 mL, 5.12 mmol) is then added and the reaction is left stirring at room temperature for 20 h. The solvent is then removed by distillation under vacuum heating at 36° C. and sterile water (5 mL) is added to the residue. A yellow precipitate is formed and the suspension is brought to pH 7 by a 10% $KHSO_4$ solution in sterile water. The formed precipitated is filtered thus obtained a yellow solid (1.6 g) which is purified by chromatography on silica gel (eluant $CH_2Cl_2$/MeOH, 40:1, $R_f$ 0.16) obtaining 1.073 g (2.77 mmol) of compound (IVa) as a pale yellow powder (54% yield).

$^1$H NMR (400 MHz, DMSO, 25° C.) δ: 1.17 (t, J=7.0 Hz, 3H), 1.84-1.91 (m, 2H), 2.38 (t, J=7.4 Hz, 2H), 3.07 (t, J=7.3 Hz, 2H), 4.04 (q, J=7.0 Hz, 2H), 4.89 (s, 2H), 6.63 (br s, 2H), 7.24-7.32 (m, 5H), 10.3 (br s, 1H).
$^{13}$C NMR (100.4 MHz, DMSO, 25° C.) δ: 15.0 (q), 25.8 (t), 30.3 (t), 32.5 (t), 43.4 (t), 60.7 (t), 101.3 (s), 128.3 (d), 128.5 (d, 2C), 129.4 (d, 2C), 138.1 (s), 147.9 (s), 148.9 (s), 152.7 (s), 162.0 (s), 173.3 (s). MS (ESI-MS) m/z (%): C18H21N5O3S, 388 (M$^+$+1, 24), 342 (100).
Mp=123-127° C.

Step (b)—Procedure for the preparation of 4-(6-Amino-9-benzyl-8-hydroxy-9H-purin-2-ylsulfanyl)-butyric Acid (Va)

In a 50 mL flask, compound (IVa) (0.421 g, 1.09 mmol) is partially dissolved in 23 mL of a 3:1 mixture of MeOH and sterile water. KOH (0.184 g, 3.77 mmol) is then added which results in the complete solubilization of the starting material. The reaction is left under stirring at 25° C. for 48 h. After that time, the solution appears clear and dark yellow. After removing the MeOH under vacuum, the residual aqueous solution is acidified to pH 3 with a 10% solution of $NaHSO_4$ in sterile water thus obtaining a pale yellow precipitate. This is filtered and washed with a slightly acid aqueous solution, then with water and finally with dichloromethane. The product is then dried under vacuum thus obtaining 274 mg (0.76 mmol) of product (Va) (70% yield).

$^1$H NMR (400 MHz, DMSO, 25° C.) δ: 1.85-1.92 (m, 2H), 2.36 (t, J=7.4 Hz, 2H), 3.08 (t, J=6.6 Hz, 2H), 4.92 (s, 2H), 6.54 (br s, 2H), 7.28-7.36 (m, 5H), 10.1 (br s, 1H), 12.1 (br s, 1H).
$^{13}$C NMR (100.4 MHz, DMSO, 25° C.) δ: 25.7 (t), 30.4 (t), 33.6 (t), 43.5 (t), 101.3 (s), 128.4 (d), 128.6 (d, 2C), 129.4 (d, 2C), 138.0 (s), 147.8 (s), 148.9 (s), 152.7 (s), 162.1 (s), 174.9 (s).
MS (ESI-MS) m/z (%): C16H17N5O3S 360 (M$^+$+1, 6), 342 (100), 274 (17).
Mp=230° C. (dec)

Step (c)—Procedure for the preparation of 4-(6-Amino-9-benzyl-8-hydroxy-9H-purin-2-ylsulfanyl)-butyric acid 2,5-dioxo-pyrrolidin-1-yl ester (SA26-E)

In a two-necked flask, the acid (Va) (0.249 g, 0.69 mmol) is dissolved in 5.5 mL of anhydrous DMF under stirring and a nitrogen atmosphere, in the presence of molecular sieves (4 Å). DCC (dicyclohexylcarbodiimide) (157 mg, 0.76 mmol) is then added followed by N-hydroxysuccinimide (80 mg, 0.69 mol). The resulting solution is left under stirring at room temperature for 23 h. After that time, the solution appears cloudy. The solution is filtered and the solvent removed under high vacuum by heating at 33° C. The residue (490 mg) is purified by chromatography on silica gel (eluant $CH_2Cl_2$/MeOH, 40:1, $R_f$ 0.11) to give 247 mg (0.54 mmol) of SA26-E as bright yellow powder (78%).

$^1$H (DMSO, 25° C.) δ: 1.94-2.01 (m, 2H), 2.77 (t, J=7.4 Hz, 2H), 2.80 (s, 4H), 3.10 (t, J=6.6 Hz, 2H), 4.88 (s, 2H), 6.53 (s, 2H), 7.24-7.34 (m, 5H), 10.1 (s, 1H).
$^{13}$C NMR (100.4 MHz, DMSO, 25° C.) δ: 24.4 (t), 25.4 (t, 2C), 29.3 (t), 33.3 (t), 42.5 (t), 100.4 (s), 127.4 (d), 127.6 (d, 2C), 128.5 (d, 2C), 137.0 (s), 146.9 (s), 148.0 (s), 151.8 (s), 160.8 (s), 170.2 (s).
MS (ESI-MS) m/z (%): C20H20N6O5S, 457 (M$^+$+1, 6), 342 (100).
Mp=161° C. (dec)

Example 2

General Procedure for the Preparation of a Conjugate Having Formula (II) Between the Active Ester SA26-E and the Protein Der p2

In a glass vial, the allergen nDer p2 (750 μg) is dissolved in 0.5 mL of a 0.1 M phosphate buffer at pH 7.4. The active ester (see Table), dissolved in DMSO (130 μL), is diluted to 1 mL with the same phosphate buffer and transferred into the vial containing the allergen (for a final volume of 1.5 mL). The solution is left under mechanical stirring at 4° C. for 18 h, and then is dialyzed.

Figure 12:
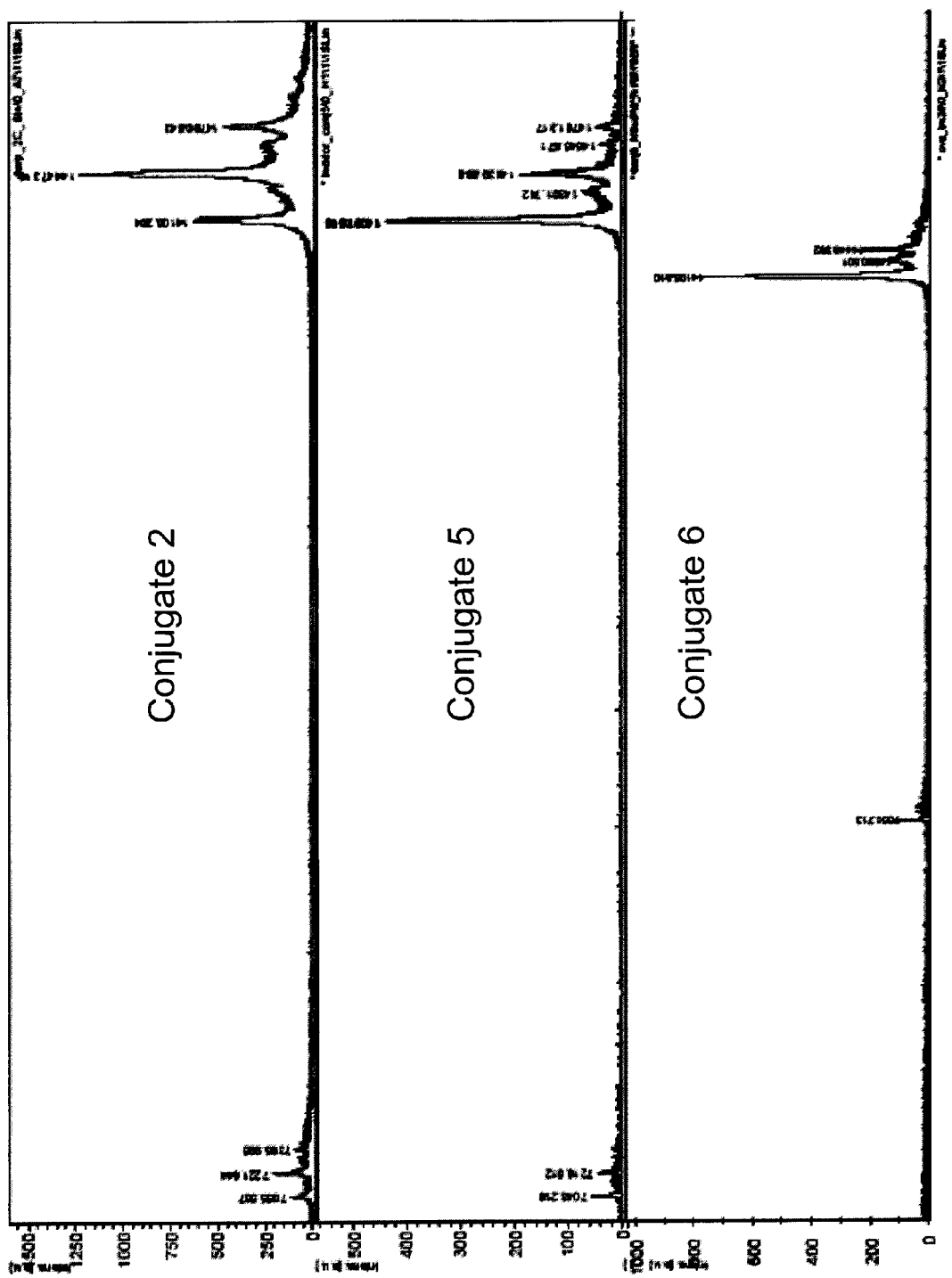
FIG. 12 show the mass spectroscopy analysis through MALDI-TOF of the conjugates 2-5 and 6 formed by nDer p2 and active ester SA-26E.

The conjugation with the protein nDer p2 is carried out by employing an excess of active ester compared to the moles of lysine evaluated to be present on the amount of the protein used, as reported in the Table. The actual conjugation has been demonstrated by a MALDI-TOF analysis of the conjugates by which it is possible to observe the presence of the unconjugated protein (14.098 KDa) and the formation of conjugates having molecular masses of 14.439 and 14.781 KDa. These are present in a variable relative amount depending on the excess of active ester employed and correspond to the protein linked to one and two modified adenine fragments, respectively, having molecular mass of 341 (see FIG. 12).

|  | Active ester (μg) | Molar ration between active ester and lysine residues | % conjugate P + 1 molecule | Conjugate P + 2 molecules |
| --- | --- | --- | --- | --- |
| Conj 1 | 1100 | 7.5 | Nd | nd |
| Conj 2 | 1100 | 7.5 | 50 | 20 |
| Conj 3 | 1100 | 7.5 |  |  |
| Conj 4 | 1100 | 7.5 |  |  |
| Conj 5 | 250 | 1.7 | 23 | 4 |
| Conj 6 | 250 | 1.7 |  |  |
| Conj 7 | 250 | 1.7 |  |  |
| Conj 8 | 250 | 1.7 |  |  |

As an example of conjugation with an allergenic protein the coupling procedure between detoxified purified natural Der p2 (nDer) is shown. The conjugation with the other allergenic proteins such as Ovalbumin (OVA), DP extract or rDer has been realized following the same procedure but varying the amount of active ester on the basis of the numbers of lysine residues present in the protein molecule which can be potentially functionalized. In the case of nDer p2 (MW 14 KDa) six different lysines are present on the molecule and the amount of active ester suitable to obtain a ratio 1.7 or 7.5 between the moles of active ester and those of lysine residues on the protein has been used. In the following tables nDer p2-conj is referred to a conjugate obtained by the use of a ratio between the moles of active ester and lysines as 1.7, Conj-5. The ratio 1.7 has been also used in the conjugation of the other allergenic proteins OVA, DP and rDer to obtain the conjugates DP-conj, OVA-conj and rDer-conj. When the ratio between the moles of active ester and those of lysine is 1.7 and the allergenic protein used is nDer p2 (such as in the conjugates Conj-5, Conj-6, Conj-7 and Conj-8), it has been calculated that, every 10 μg conjugate, the amount of active ester actually present is 0.085 μg. Thus 0.085 μg/ml SA-26E has been thus used alone or mixed with 10 μg/ml nDer p2 as control in some of the experimental models.

Example 3

Evaluation of the Production of Innate Cytokines and Chemokines

Step (a)—Procedure for Stimulation of Cells from the Innate Immunity and Determination of Innate Cytokines and Chemokines Circulating mononuclear cells (MNC) are isolated by density gradient (Ficoll-Hypaque) using buffy coats from 14 normal donors (Servizio Immunotrasfusionale e terapie cellulari, Azienda Ospedaliera Universitaria A. Meyer, Firenze). $200\times10^6$ MNC are separated by the use of a commercial kit (CD14 isolation kit, Miltenyi) by the addition of 400 μl anti-CD14 monoclonal antibody bound to iron beads followed by isolation on magnetic columns (LS column). $50\times10^6$ monocytes are recovered by positive selection and are extensively washed with calcium and magnesium-free sterile PBS and then seeded in complete medium plus 10% foetal calf serum in 24 flat bottomed plates at the concentration of $1\times10^6$/ml. As stimulants, the following compounds have been used: unconjugated allergens (DP or nDer) (10 μg/ml), their respective conjugates (DP-conj or nDer p2-conj) (10, 2.5 and 0.6 μg/ml), R-848 (2 μg/ml, 6 μM), SA-26, SA-26A or SA-26E (10, 2.5 and 0.6 μg/ml), LPS (100 ng/ml) and CpG-ODN 2006 (10 μg/ml, 1.3 μM). The plates are incubated for 36 hrs at 37° C. in 5% $CO_2$ humidified atmosphere and the supernatants are collected after centrifugation at 1200 rpm, aliquoted and then stored at −20° C. up to the assay.

The preparation of purified BDCA4+ cells has been obtained in a similar way starting from MNC of buffy coats of the same 14 healthy donors. After density gradient separation, $500\times10^6$ MNC have been isolated by the use of a commercial kit (BDCA4 isolation kit, Miltenyi) by addition of 500 μl anti-BDCA4 monoclonal antibody bound to iron beads followed by separation on magnetic columns (LS column). By positive selection $5\times10^6$ plasmacytoid dendritic cells (PDCs) are recovered, extensively washed with calcium and magnesium-free sterile PBS and seeded in complete medium plus 10% foetal calf serum in 24-flat bottomed plates at the concentration $1\times10^6$/ml. As stimulants, the following compounds have been used: unconjugated allergens (DP or nDer) (10 μg/ml), their respective conjugates (DP-conj or nDer p2-conj) (10, 2.5 and 0.6 μg/ml), R-848 (2 μg/ml, 6 μM), SA-26, SA-26A or SA-26E (10, 2.5 and 0.6 μg/ml), LPS (100 ng/ml) and CpG-ODN 2006 (10 μg/ml, 1.3 μM). The plates are incubated for 36 hrs at 37° C. in 5% $CO_2$ humidified atmosphere and the supernatants are collected after centrifugation at 1200 rpm, aliquoted and then stored at −20° C. up to the assay.

$1\times10^5$ cells have been devoted to check the purity of the preparation and have been incubated in ice with 20 μl fluorochrome-conjugated anti-CD14 or anti-BDCA4 monoclonal antibodies in the dark. Cells are then washed with PBS, centrifuged, resuspended with 500 μl PBS and then analyzed at FACS. Purity was always above 98%.

For the determination of cytokines and chemokines of the innate immunity, commercial ELISAs have been used: IL-12p40 (Cytoscreen, Biosource Int, Camarillo, Calif.), IFN-alfa (Cytoscreen), TNF-alfa (Cytoscreen), IL-10 (Pharmingen), IL-6 and CXCL10 (R&D System). 100 μl/well of single supernatants are incubated in flat bottomed plates as specified by the productors and the amounts of the single cytokines are expressed as pg/ml on the basis of a reference curve by using recombinant cytokines.

The addition of LPS on purified CD14+ cells [Example 3 (step a)] stimulates, as expected, the production of relevant amounts of modulatory (IL-12) and inflammatory (TNF-alfa and IL-6) cytokines at levels similar to those obtained by the use of SA-26. On the contrary, the adenine SA-26A is unable to activate the production of any cytokine independently of the dose used and the soluble modified adenine SA-26E has an intermediate effect. The addition of 0.085 µg/ml soluble SA-26E (that is, as already specified, the corresponding amount of active ester present in Conj-5, -6, -7 and -8) is not able to stimulate the production of any cytokine. The unconjugated allergens (DP extract and nDer p2) are essentially unable to induce the production of valuable cytokines from purified CD14+ cells. However, after conjugation with SA-26E, both the allergenic molecules (DP-conj and nDer p2-conj) induce significant amounts of modulatory and regulatory cytokines at similar levels than those induced by other stimulants, even when used at low concentrations. The production of other cytokines such as IL-27 or the regulatory molecule MO is never observed (data not shown).

Analogously, BDCA4+ cells from the same donors are able to produce high levels of IFN-alfa, IL-10 and CXCL10 in response to R-848 whereas the adenine SA-26A is not able to induce any cytokine production. On the other hand, SA-26E exerts an intermediate effect on plasmacytoid dendritic cells depending on the dose used. However, SA-26E is completely inactive when used at 0.085 µg/ml concentration. As expected, unconjugated allergens do not stimulate cytokine production, whereas conjugated allergens DP-conj and nDer p2-conj induce the production of high levels of both IFN-alfa and IL-10. Neither IL-29 or CXCL10 production are significantly modified by the addition of any of the stimulants with the only exception of R-848 (data not shown).

The following tables show the results (mean±SE) obtained from stimulated CD14+ (Tables A and B) and BDCA4+ (Tables C and D) cells with the corresponding significance.

TABLE A

Cytokine production by purified CD14+ cells

| Condition | Dose (µg/ml) | IL-12p40 | TNF-alfa | IL-6 | IL-10 |
|---|---|---|---|---|---|
| Donor #1 | | | | | |
| Medium |  | 0 | 0 | 0 | 0 |
| LPS |  | 2725 | 5331 | 12905 | 8140 |
| SA-26 | 10 | 3120 | 1635 | 1508 | 296 |
|  | 2.5 | 1949 | 817 | 1713 | 280 |
|  | 0.6 | 446 | 367 | 67 | 290 |
| SA-26A | 10 | 0 | 0 | 0 | 0 |
|  | 2.5 | 0 | 0 | 0 | 0 |
|  | 0.6 | 0 | 0 | 0 | 0 |
| SA-26E | 10 | 2500 | 2123 | 2930 | 609 |
|  | 2.5 | 863 | 597 | 11 | 618 |
|  | 0.6 | 569 | 345 | 0 | 124 |
|  | 0.085 | 0 | 0 | 0 | 0 |
| Donor #2 | | | | | |
| Medium |  | 0 | 0 | 0 | 0 |
| LPS |  | 6311 | 4619 | 3125 | 1155 |
| SA-26 | 10 | 7678 | 2450 | 1713 | 258 |
|  | 2.5 | 5451 | 2353 | 1457 | 243 |
|  | 0.6 | 1187 | 597 | 248 | 209 |
| SA-26A | 10 | 0 | 0 | 0 | 0 |
|  | 2.5 | 0 | 0 | 0 | 0 |
|  | 0.6 | 0 | 0 | 0 | 0 |
| SA-26E | 10 | 4800 | 3730 | 163 | 584 |
|  | 2.5 | 2464 | 1267 | 4 | 243 |
|  | 0.6 | 785 | 466 | 0 | 0 |
|  | 0.085 | 0 | 0 | 0 | 0 |

TABLE B

Cytokine production by purified CD14+ cells

| Condition | Dose (µg/ml) | IL-12p40 | TNF-alfa | IL-6 | IL-10 |
|---|---|---|---|---|---|
| Medium |  | 0 ± 0 | 0 ± 0 | 0 ± 0 | 0 ± 0 |
| LPS | 1 | 3.8 ± 1.7** | 7.6 ± 2.7** | 17.5 ± 4.9*** | 7.9 ± 1.9* |
| R-848 | 2 | 16.9 ± 6.3*** | 16.3 ± 4.9**** | 45.8 ± 15.2*** | 2.0 ± 0.5*** |
| DP | 10 | 0.05 ± 0.07 | 0.06 ± 0.05 | 0.1 ± 0.2 | 0 ± 0 |
| DP-conj | 10 | 6.4 ± 1.3**** | 5.5 ± 1.1**** | 24.4 ± 8.8*** | 1.0 ± 0.2*** |
|  | 2.5 | 2.9 ± 1.2** | 1.8 ± 0.6** | 9.7 ± 5.0* | 0.4 ± 0.1* |
|  | 0.6 | 0.7 ± .01*** | 0.5 ± 0.2** | 0.3 ± 0.4 | 0.1 ± 0.08 |
| nDer p2 | 10 | 0 ± 0 | 0.05 ± 0.06 | 0 ± 0 | 0.4 ± 0.4 |
| nDer p2-conj | 10 | 0.8 ± 0.15**** | 0.9 ± 0.2*** | 2.1 ± 1.4* | 0.1 ± 0.1 |
|  | 2.5 | 0.7 ± 0.2* | 0.5 ± 0.2* | 0.06 ± 0.05 | 0.25 ± 0 |
|  | 0.6 | 0.14 ± 0.08 | 0.05 ± 0.06 | 0 ± 0 | 0 ± 0 |

P values:

*<0.05,

**<0.005,

***<0.0005,

****<0.00005

TABLE C

Cytokine production by purified BDCA4+ cells

| Condition | Dose (µg/ml) | IFN-alfa | TNF-alfa | IL-6 | IL-10 |
|---|---|---|---|---|---|
| Donor #1 | | | | | |
| Medium | | 254 | 0 | 0 | 0 |
| R-848 | | 3154 | 10368 | 746 | 1500 |
| SA-26A | 10 | 0 | 268 | 0 | 0 |
| | 2.5 | 0 | 0 | 0 | 0 |
| | 0.6 | 0 | 2 | 0 | 0 |
| SA-26E | 10 | 486 | 858 | 675 | 896 |
| | 2.5 | 179 | 252 | 0 | 0 |
| | 0.6 | 179 | 183 | 0 | 0 |
| | 0.085 | 0 | 0 | 0 | 0 |
| Donor #2 | | | | | |
| Medium | | 0 | 0 | 0 | 0 |
| R-848 | | 6187 | 20990 | 308 | 753 |
| SA-26A | 10 | 168 | 531 | 0 | 0 |
| | 2.5 | 161 | 1 | 0 | 0 |
| | 0.6 | 0 | 2 | 0 | 0 |
| SA-26E | 10 | 3589 | 3405 | 1439 | 750 |
| | 2.5 | 2014 | 1157 | 760 | 209 |
| | 0.6 | 669 | 520 | 0 | 0 |
| | 0.085 | 0 | 0 | 0 | 0 |

TABLE D

Cytokine production by purified BDCA4+ cells

| Condition | Dose (µg/ml) | IFN-alfa | TNF-alfa | IL-6 | IL-10 |
|---|---|---|---|---|---|
| Medium | | 0.1 ± 0.1 | 0 ± 0 | 0 ± 0 | 0 ± 0 |
| R-848 | 2 | 5.6 ± 2.5** | 5.4 ± 1.4**** | 7.7 ± 2.6*** | 1.0 ± 0.6* |
| DP | 10 | 0.1 ± 0.1 | 0.01 ± 0.01 | 0 ± 0 | 0 ± 0 |
| DP-conj | 10 | 6.5 ± 2.2*** | 3.9 ± 1.3*** | 9.8 ± 4.8** | 1.4 ± 0.7* |
| | 2.5 | 11.8 ± 1.6**** | 1.6 ± 0.5*** | 5.1 ± 2.6* | 0.5 ± 0.15** |
| | 0.6 | 9.0 ± 1.6*** | 0.6 ± 0.1** | 1.3 ± 05 | 0.1 ± 0.1 |
| nDer p2 | 10 | 0.07 ± 0.06 | 0.03 ± 0.02 | 0 ± 0 | 0 ± 0 |
| nDer p2-conj | 10 | 2.2 ± 1.9* | 1.5 ± 0.3*** | 2.0 ± .7* | 0.5 ± 0.12** |
| | 2.5 | 1.05 ± 0.25* | 1.0 ± 0.1*** | 1.0 ± 0.5 | 0.2 ± 0.08 |
| | 0.6 | 0.8 ± 0.07*** | 0.23 ± 0.02** | 0.1 ± 0.1 | 0.04 ± 0.04 |

P values:
*<0.05,
**<0.005,
***<0.0005,
****<0.00005

To verify that the allergenic protein conjugated with the active ester SA-26E is indeed able to exhibit a modulatory activity higher than the simple mixture of the allergenic protein itself plus soluble SA-26E, purified CD14+ and BDCA4+ cells from two healthy donors have been cultured for 36 hrs in the presence of the native allergenic protein nDer p2 (10 µg/ml), the conjugated compound nDer p2-conj (Conj-5), LPS or R-848 (100 ng/ml and 2 µg/ml, respectively) or with the mixture nDer p2 and soluble SA-26E (10 µg/ml and 0.085 µg/ml respectively) in order to stimulate the production of modulatory, regulatory and pro-inflammatory cytokines. Both the unconjugated allergen, as expected, but also the mixture between the allergen and soluble active ester are unable to stimulate the production of significant amounts of cytokines from monocytes or plasmacytoid dendritic cells. Only when the allergen was conjugated together the modified adenine, relevant amounts of cytokines similar to those obtained by the use of known immunomodulatory agents such as LPS and R-848 were obtained.

The following tables (E and F) show the data obtained in the two donors.

TABLE E

Cytokine production from purified CD14+ cells

| Stimulus | Dose (µg/ml) | IL-12p40 | TNF-alfa | IL-6 | IL-10 |
|---|---|---|---|---|---|
| Donor #1 | | | | | |
| Medium | | 0 | 0 | 0 | 0 |
| LPS | 0.1 | 5627 | 3136 | 27235 | 530 |
| nDer p2 | 10 | 0 | 218 | 0 | 0 |
| nDer p2-conj (Conj-5) | 10 | 2167 | 892 | 10784 | 706 |
| nDer p2 + soluble SA-26E | 10 + 0.085 | 371 | 15 | 22 | 0 |
| Donor #2 | | | | | |
| Medium | | 0 | 4 | 0 | 0 |
| LPS | 0.1 | 10522 | 14061 | 39499 | 3000 |
| nDer p2 | 10 | 0 | 0 | 0 | 0 |
| nDer p2-conj (Conj-5) | 10 | 9086 | 3421 | 17715 | 2144 |
| nDer p2 + soluble SA-26E | 10 + 0.085 | 466 | 299 | 10 | 0 |

TABLE F

Cytokine production from BDCA4+ cells

| Stimulus | Dose (µg/ml) | IFN-alfa | TNF-alfa | IL-6 | IL-10 |
|---|---|---|---|---|---|
| Donor #1 | | | | | |
| Medium | | 0 | 0 | 0 | 0 |
| R-848 | 2 | 1131 | 4832 | 44302 | 1864 |
| nDer p2 | 10 | 0 | 0 | 0 | 0 |
| nDer p2-conj (Conj-5) | 10 | 2233 | 2008 | 12152 | 6375 |
| nDer p2 + SA-26E solubile | 10 0.085 | 0 | 0 | 0 | 0 |
| Donor #2 | | | | | |
| Medium | | 29 | 0 | 0 | 0 |
| R-848 | 2 | 1605 | 6898 | 37603 | 1305 |
| nDer p2 | 10 | 0 | 0 | 0 | 0 |

TABLE F-continued

Cytokine production from BDCA4+ cells

| Stimulus | Dose (μg/ml) | Cytokine production (pg/ml) | | | |
|---|---|---|---|---|---|
| | | IFN-alfa | TNF-alfa | IL-6 | IL-10 |
| nDer p2-conj (Conj-5) | 10 | 1443 | 4550 | 17667 | 2429 |
| nDer p2 + SA-26E solubile | 10 + 0.085 | 326 | 0 | 0 | 0 |

Examples 4

Evaluation of the Binding of Conjugated Products to Receptors and Stimulation of Second Messengers Step (a) Procedure for the Evaluation of NF-κB Activation $5 \times 10^6$ purified CD14+ cells were cultured in polypropylene 15 ml tubes in complete medium plus 10% foetal serum in the presence of the following products as stimulants: unconjugated allergens (DP or nDer) (10 μg/ml), their respective conjugates (DP-conj or nDer p2-conj) (10 μg/ml), R-848 (2 μg/ml) or nDer p2 mixed together with soluble SA-26E (10 μg/ml and 0.085 μg/ml respectively). The tubes are then incubated for 2 hrs in 5% $CO_2$ humidified atmosphere at 37° C. and then washed with 10 ml PBS, centrifuged at 1500 rpm repeating the treatment thrice and the cellular pellet finally dried by the use of a micropipette and stored at −80° C. up to the assay. The nuclear extract of the cultured cells was prepared by the addition of a mixture of reactive compounds to single tubes following the instruction (Active Motif) and the protein content of the single preparations was evaluated by Bradford method. Two different protein amounts (0.5 and 2 μg) were incubated in 96w plates coated by the immobilized oligonucleotide containing the activated NF-κB consensus site (5'-GGGACTTTCC-3'), followed by the incubation with an antibody recognizing an epitope of the NF-κB p50 subunit. An HRP-conjugated secondary antibody was added to single wells and the colorimetric read-out was quantified by spectrophotometry. Values are reported as Optical Density. As positive control, Jurkat nuclear extract was used as suggested by the manufacturer. For the specificity of the assay, a wild-type consensus oligonucleotide was used as a competitor for NF-κB binding.

Step (b) Procedure to Monitor TLR7 Activation

HEK293 cells are detached by trypsin from the plastic surface of the culture bottle, extensively washed with calcium and magnesium-free PBS, counted and adjusted at the concentration $1 \times 10^6$ cells/tube in polypropylene V-bottomed tubes. After the final wash, the cells are pelleted and 100 μl transfection buffer (Amaxa) is added together with 5 μTLR3, TLR7, TLR8 or TLR9-encoding and ELAM-1 promoter NF-kB luciferase reporter plasmids. The mixture thus obtained is transferred in special cuvettes and transient transfection is obtained in a special apparatus which is able to directly introduce genetic material into the nucleus (Nucleofection®, Amaxa GmbH). The cells are then recovered and cultured at $1 \times 10^5$/ml in 48-flat bottomed plates in E-MEM medium plus 5% foetal calf serum for 18 hrs. After this first incubation, medium (as negative control) or the following compounds as stimulants are added for additional 18 hrs: DP, nDer p2 or their respective conjugates DP-conj or nDer p2-conj (10 μl/ml), nDer p2 mixed with soluble SA-26E (10 μg/ml and 0.085 μg/ml respectively) or already known TLR-ligands such as Poly I:C (50 μg/ml), R-848 (2 μg/ml) or CpG-ODN 2006 (1.3 μM). Finally the luciferase activity is measured in the cellular lysates by a commercial kit (Promega).

The conjugated allergens DP-conj and nDer p2-conj but not the unconjugated allergens DP and nDer p2 which are actually inactive, are able to induce a significant increase in the p50 nuclear expression in purified CD14+ cells [Example 4 (step a)] exhibiting a similar effect as R-848 that exerts, as expected, a rapid and high activation of p50 even higher than the positive control itself (Jurkat cells). The effects exerted by conjugated compounds suggest that the conjugates are able to activate the NF-κB signalling pathway.

In FIG. 1 a representative case is shown.

On transfected HEK293 cells along with the method used as indicated in [Example 4 (step b)], we have also found, as expected, that R-848 and CpG-ODN 2006 are able to induce NF-κB expression in TLR7/8 and TLR9-transfected cells, respectively, whereas Poly I:C activates TLR3-expressing cells (data not shown). The unconjugated allergenic proteins DP and nDer p2 lack any activity. In addition, the mixture nDer p2 and soluble SA-26E (10 μg/ml and 0.085 μg/ml respectively) is completely inactive (data not shown). Similar effects are obtained when HEK293 cells are transfected by the use of a murine TLR7-encoding plasmid together with ELAM-1 promoter NF-kB luciferase reporter.

Figure 2A:
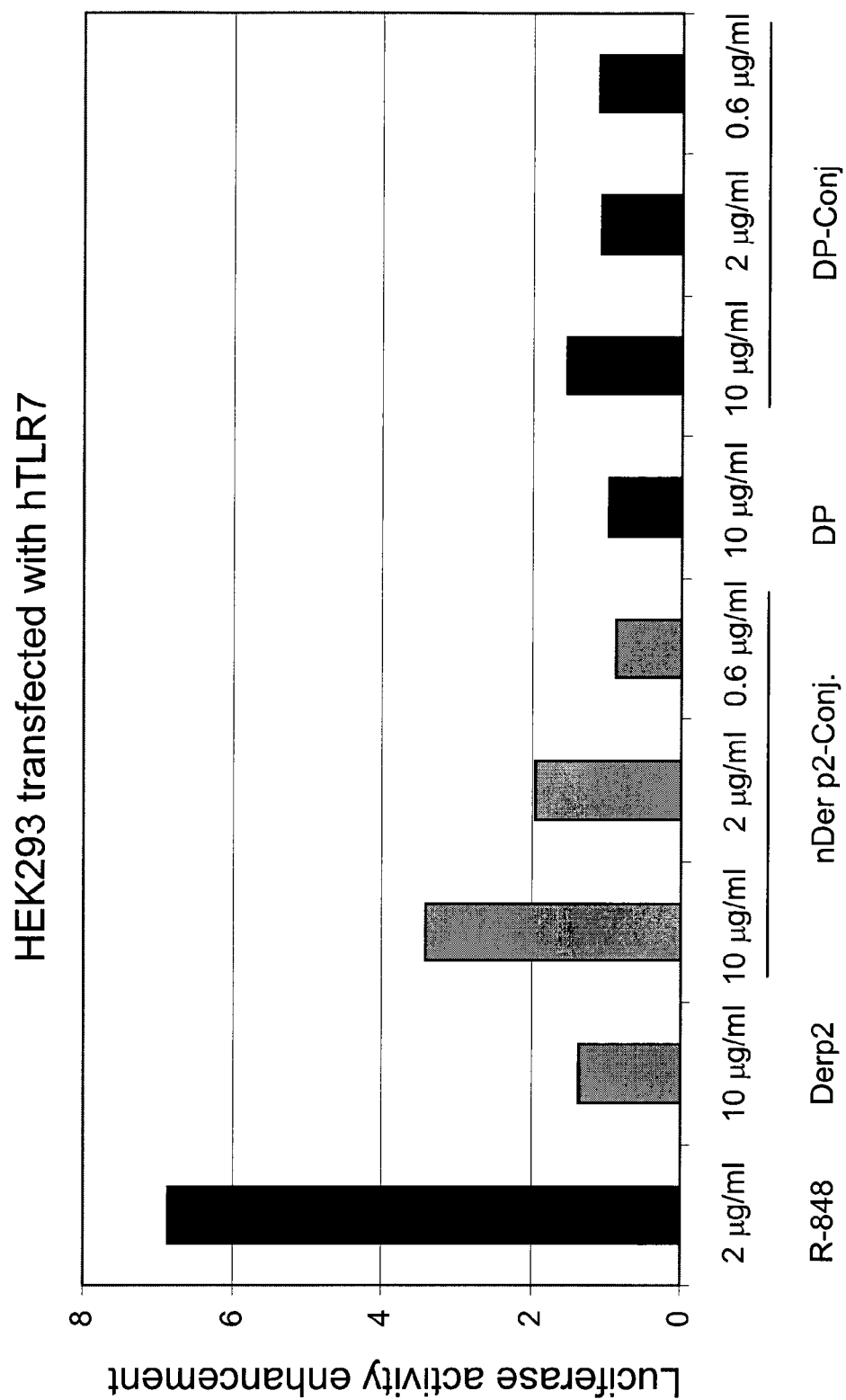
FIG. 2 shows the increase in luciferase activity in co-transfected HEK293 cells by means of Nucleofector® with human (FIG. 2A) or murine (FIG. 2B) TLR7-encoding plasmids together with an ELAM-1 promoter NF-kB luciferase reporter plasmid. Transfected cells have been then stimulated by the use of an already known TLR7-ligand, R-848 (2 μg/ml, 6 μM) used as positive control, or the native allergenic proteins nDer p2 or DP extract, or their respective conjugates nDer p2-conj (Conj-5) or DP-conj in a dose-dependent manner (10-2-0.5 µg/ml) or medium alone as negative control as specified in the Example 4 (step b). The increase in the luciferase activity (y-axis) is expressed as index of increase in comparison with the negative control. Two representative experiments are shown.
Figure 2B:
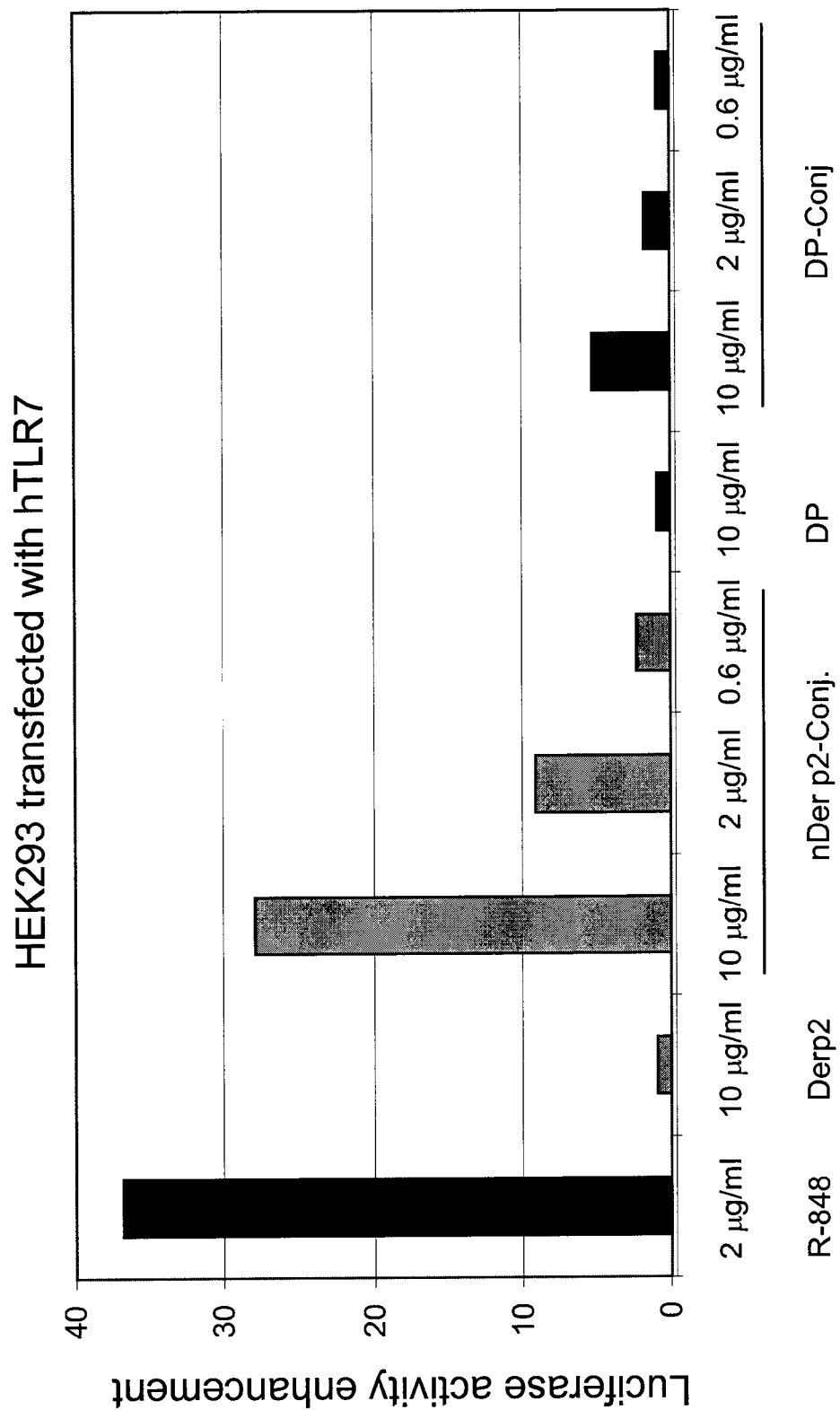

FIGS. 2A and 2B show the data obtained in these experiments (one representative experiment).

Example 5

Evaluation of the Effect on the T Cell Phenotype

Step (a) Procedure to Monitor the Functional Phenotype of Allergen-Specific T Cell Lines Mononuclear cells from 10 atopic donors with sensitization towards Dermatophagoides pteronyssinus have been isolated by density gradient and $1 \times 10^6$ cells cultured in 2 ml complete medium plus 5% autologous serum in the presence of DP or nDer p2 allergens or their respective conjugates (DP-conj or nDer p2-conj) (all at 10 μg/ml) in 24 flat-bottomed plates (Costar). As positive control, cells are also cultured in the presence of DP or nDer p2 and soluble R-848 (2 μg/ml). After 6 d incubation and addition of rIL-2 (Proleukin) (25 UI/ml), T cell blasts are further expanded by the addition of medium, fresh 5% autologous serum and 25 UI/ml rIL-2 every three days. After 15 d culture, T cell blasts from single cultures are collected, washed with sterile PBS, counted and used to assess allergen specificity, phenotype and function.

To assess allergen-specificity, $1 \times 10^5$ T cell blasts are cultured in 96 U-bottomed plates in 0.2 ml final volume in medium plus 5% autologous serum, $1 \times 10^5$ autologous irradiated (9000 R) mononuclear cells as APCs, DP or nDer p2 (10 μg/ml) and, after 3 d incubation, tritiated thymidine (3HTdR) (Amersham) is added. After further 16 hr incubation, single cultures are transferred on paper filters through the use of an Harvester apparatus (Tomtec) and radioactivity measured in a β-counter. T cell lines are considered as specific when stimulation index (SI) (cpm in cultures stimulated in the presence of autologous MNC plus allergen/cpm in cultures in the presence of autologous MNC alone) is above 3 as already published (Brugnolo F et al J Allergy Clin Immunol 2003 February; 111(2): 380-9; Filì L et al, J Allergy Clin Immunol 2006 August; 118(2):511-7).

For phenotypic analysis, $2\times10^5$ T cell blasts are resuspended in PBS 0.5% BSA and 0.02% sodium azide and treated with rabbit IgG to saturate unspecific sites. Cells are then incubated for 20 min with anti-CD3, anti-TCRαβ, anti-TCRγδ, anti-CD4, anti-CD8, anti-CD16, anti-CD20 and anti-CD56 monoclonal antibodies (Becton-Dickinson) or their respective isotype control antibodies (Southern Biotechnologies). At the end of the incubation, cells are washed and analysed at FACSCalibur (Becton-Dickinson) acquiring at least $10^4$ events for each sample. The T cell lines obtained in the presence of DP-conj and nDer p2-conj exhibit higher percentages of CD3+γδ+ and CD16+CD56+ than unconjugated-specific T cell lines but similar to TCL derived in the presence of R-848.

To functionally analyze the T cell blasts, the following parameters have been considered: i) intracellular production of cytokines by cytofluorimetric analysis after polyclonal stimulation with PMA and ionomicin; ii) expression of transcription factors related to the $T_H1$, $T_H2$, $T_H17$ and Treg phenotypes; iii) cytokine production in the supernatants after polyclonal stimulation with PMA and anti-CD3 monoclonal antibody; iv) mRNA expression for $T_H2$- or $T_H1$-related cytokines by the use of quantitative RT-PCR.

For the analysis of the intracellular cytokine production at single cell level, $1\times10^6$ T cell blasts from T cell lines specific for DP, nDer p2 or their respective conjugates are stimulated for 4 hrs (the last two in the presence of the Golgi venom Brefeldin A 5 µg/ml) with PMA (10 ng/ml) and ionomicin (1 µM) as already described (Brugnolo F et al J Allergy Clin Immunol 2003 February; 111(2): 380-9; Filì L et al, J Allergy Clin Immunol 2006 August; 118(2):511-7). After the incubation, the cells are washed with PBS pH 7.2 and then fixed for 15 min with formaldehyde 2% in PBS, washed again with 0.5% BSA in pH 7.2 PBS and finally permeabilized with pH 7.2 PBS containing 0.5% BSA and 0.5% saponin. At the end, the cells are incubated with the specific monoclonal antibody analyzing the following cytokines: IL-4, IFN-gamma, IL-5, IL-13, IL-9 and IL-17. The analysis is done by the use of FACSCalibur and the software CellQuest (Becton-Dickinson) acquiring at least $10^4$ events in CD3+CD4+TCRαβ+ or CD3-CD16+-gated cells for each sample.

For the determination of the cytokine (IL-4, IFN-gamma, IL-5, IL-13, IL-10 and IL-17) content in the supernatants, $1\times10^6$/ml T cell blasts from allergen-specific lines are stimulated with PMA (20 ng/ml) and anti-CD3 monoclonal antibody (UCHT1, Pharmingen, 50 ng/ml) in 1 ml volume for 36 hrs. The cytokine determination is based on ELISA assays with the use of commercial pairs of antibodies as already described (Brugnolo F et al J Allergy Clin Immunol 2003 February; 111(2): 380-9; Filì L et al, J Allergy Clin Immunol 2006 August; 118(2):511-7): 11-4, IL-5 and IL-10 (BD Pharmingen, Franklin Lakes, N.J.), IL-17 and IL-13 (R&D System), IFN-gamma (Endogen, Woburn, Mass.).

The expression of transcription factors related to $T_H1$, $T_H2$, $T_H17$ and Treg (T-bet, GATA-3, ROR C and Foxp3, respectively) phenotype has been determined by the use of quantitative real-time RT-PCR.

mRNA expression of cytokines (IFN-gamma, IL-2, IL-4, IL-5, IL-9, IL-13, IL-17, TGF-beta1, IL-22, IL-27, CXCL10 and MMIF) has been determined by the use of quantitative real-time RT-PCR. In brief, total RNA is extracted from $1\times10^6$/ml T cell blasts by using the RNeasy kit and treated with Dnase I to eliminate any genomic DNA contamination (Qiagen) and quantified by NanoDrop (Celbio) in each mRNA sample. cDNA is then synthesized from the same template quantity (TaqMan Reverse Transcription Reagents, Applied Biosystems, Foster City, Calif.). Real-time polymerase chain reaction (PCR) is performed with an ABI Prism 7900HT Sequence Detection System (Applied Biosystems) and all PCR amplifications are performed by MicroAmp optical 96 well reaction plate with TaqMan Universal Master Mix and with Assay-on-Demand (Applied Biosystems). Each assay is carried out in duplicate and included a no-template sample as negative control comparing experimental levels with a standard curve generated with serial dilution of cDNA obtained from human MNCs. β-Actin is used as a housekeeping gene for normalization. Inducing allergen-specific T cell lines [Example 5 (step a)] we observed that the percentage of the cells able to produce IFN-gamma is significantly higher in the T cell lines obtained by the use of conjugated allergens DP-conj and nDer p2-conj (Conj-5) than in those derived in the presence of unconjugated native allergens DP and nDer p2 with a parallel decrease in the percentage of IL-4 producing cells. The effect of redirection of allergen-specific cells from a prevalent $T_H2$ phenotype towards a prevalent $T_H1/T_H0$ observed when conjugated allergens are used, is similar to the effect obtained when soluble R-848 together with unconjugated allergens DP and nDer p2 is added in the culture system, whereas the mixture nDer p2 and soluble SA-26E (10 µg/ml and 0.085 µg/ml, respectively) is not able to modify the cellular phenotype. No difference in the percentage of IL-9 or IL-17 producing cells is observed between allergen- or conjugated allergen-specific T cell lines. In particular, the percentage of IL-17-producing cells is very low in both conditions. Along with the reduced production of IL-4, lower percentages of IL5 and IL-13 producing cells is observed in DP-conj- and nDer p2-conj specific T cell lines in comparison with unconjugated DP- or nDer p2-specific TCLs (data not shown).

Figure 3:
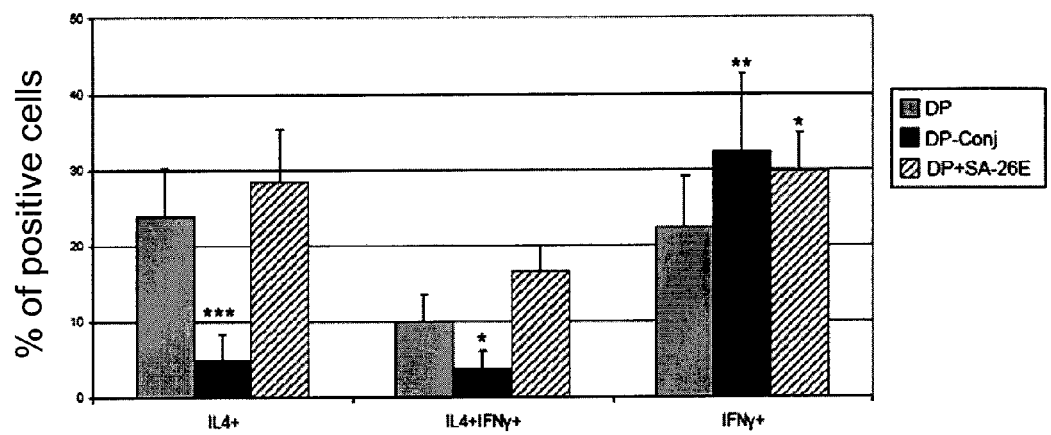
FIG. 3 shows the intracellular expression of IL-4 and IFN-gamma by T cell lines specific for DP extract (grey columns) or its respective conjugate DP-conj (black columns) (both at 10 µg/ml) after polyclonal stimulation with PMA and ionomicin as detailed in Example 5 (step a). Striped columns show the results obtained by the use of the allergenic molecule DP mixed with soluble SA-26E at the concentration of 0.085 µg/10 µg of allergen (amount of SA-26E present in Conj-5). In the figures the percentages (mean±SE) of CD3+CD4+ cells able to express IL-4 alone ($T_H2$ cells), IFN-gamma alone ($T_H1$ cells) or both cytokines ($T_H0$ cells) are shown. Significance has been evaluated by t-Student test.
Figure 4:
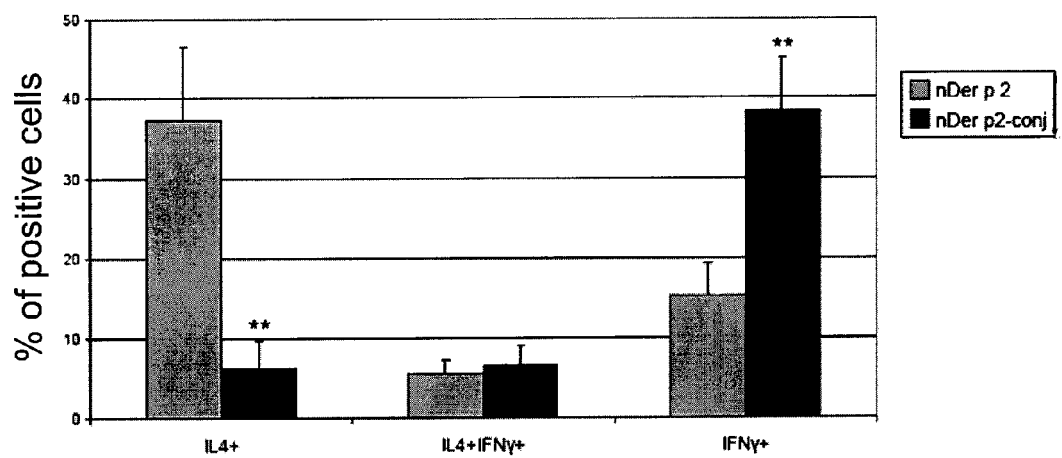
FIG. 4 shows the intracellular expression of IL-4 and IFN-gamma by T cell lines specific for the purified allergen nDer p2 (grey columns) or its respective conjugate nDer p2-conj (Conj-5) (black columns) (both at 10 µg/ml) after polyclonal stimulation with PMA and ionomicin as detailed in Example 5 (step a). In the figures the percentages (mean±SE) of CD3+CD4+ cells able to express IL-4 alone ($T_H2$ cells), IFN-gamma alone ($T_H1$ cells) or both cytokines ($T_H0$ cells) are shown (14 donors). Significances have been evaluated by t-Student test.

FIGS. 3 and 4 show the mean (±SE) of the percentages of CD3+CD4+ cells specific for DP or DP-Conj (FIG. 3) and nDer p2 or their respective conjugates (FIG. 4) able to produce IL-4, IFN-gamma or both cytokines (mean of 10 different donors).

These results are even confirmed by the determination of the cytokine content into the supernatants. T cell blasts from T cell lines specific for DP-conj or nDer p2-conj (Conj-5) produce significantly lower amounts of the $T_H2$-related cytokines (IL-4, IL-5, IL-13) and significantly higher levels of IFN-gamma than TCLs specific for unconjugated DP and nDer p2. We have never observed the production of significant amounts of IL-17 (data not shown).

Analogously, quantitative real-time RT-PCR shows that T cell lines obtained in the presence of the conjugated allergens DP and nDer p2-conj are able to express significantly higher levels of IFN-gamma (and significantly lower of IL-4, IL-5 and IL-13) than TCLs specific for the unconjugated allergens DP and nDer p2. No difference in the production of IL-10, IL-29, IL-17, IL-22, TGF-beta1, CXCL10 or MMIF was observed.

Figure 5:
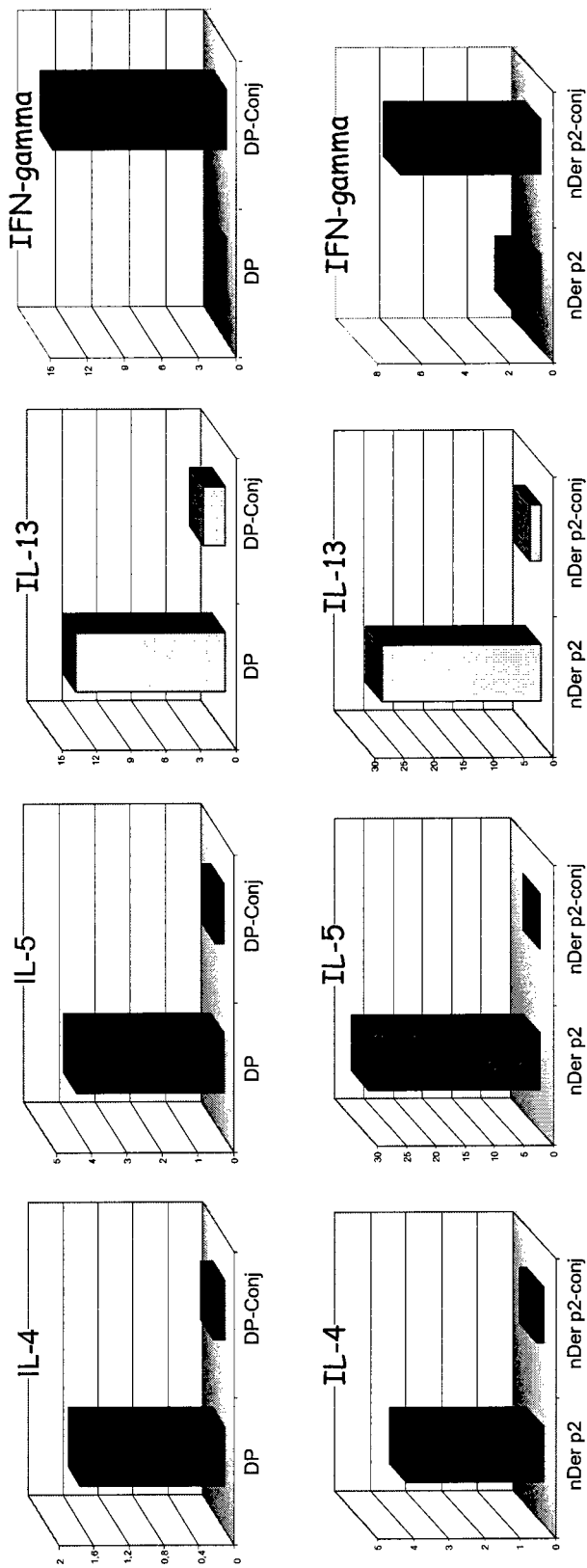
FIG. 5 shows mRNA expression levels of cytokines related to the $T_H2$ (IL-4, IL-5 and IL-13) or $T_H1$ (IFN-gamma) phenotype by the use of quantitative real time RT-PCR in T lymphocytes from cell lines specific for the allergenic DP extract and its respective conjugate DP-conj (upper panel) or the purified allergen nDer p2 and its respective conjugate nDer p2-conj (Conj-5) (lower panel) as specified in the Example 5 (step a). On the y-axis the increase index in comparison with the reference gene for β-actin is shown. In the Figure a representative case is shown.

In the FIG. 5 a representative case is shown.

The redirection of allergen-specific T cell lines from the $T_H2$ towards the $T_H1/T_H0$ phenotype is finally confirmed also at transcriptional level. Actually T cell lines derived in the presence of DP-conj and nDer p2-conj express higher levels of the $T_H1$-related transcription factor T-bet and lower levels of GATA-3 than T cell lines specific for the unconjugated allergens DP or nDer p2. We have never observed differences in the expression of $T_H17$-related RoRC transcription factor. Analogously, no modification in the expression of the Treg-related transcription factor Foxp3 is found.

In all the experiments, the mixture between nDer p2 and soluble SA-26E (10 µg/ml and 0.085 µg/ml, respectively) is completely inactive (data not shown).

Figure 6:
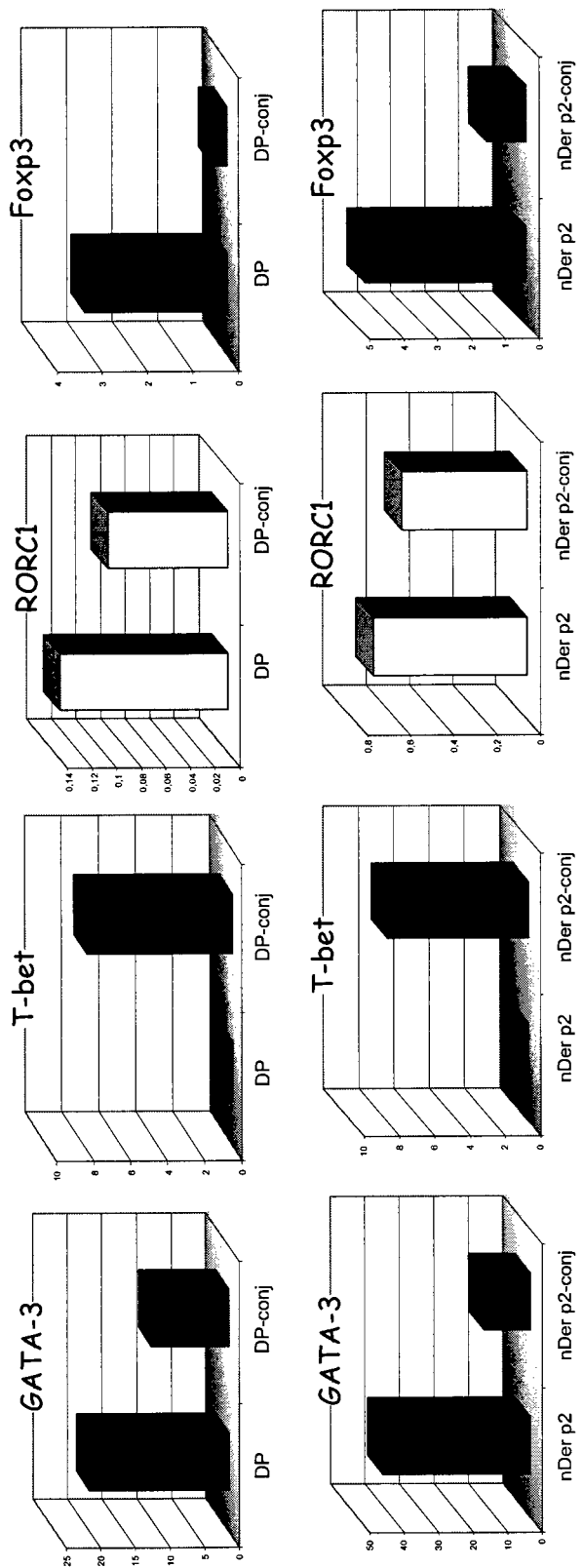
FIG. 6 shows mRNA expression levels of transcription factors related to the $T_H2$ (GATA-3), $T_H1$ (T-bet), $T_H17$ (ROR C) or regulatory (Foxp3) phenotype by the use of quantitative real time RT-PCT in T cell lines specific for the allergenic DP extract and its respective conjugate DP-conj (upper panel) or the purified allergen nDer p2 and its respective conjugate nDer p2-conj (Conj-5) (lower panel) as specified in the Example 5 (step a). On the y-axis the increase index in comparison with the reference gene for β-actin is shown. In the Figure a representative case is shown.

The results are shown in FIG. 6 (one representative case).

Step (b) Procedure to Monitor if the Functional
Phenotype of Allergen-Specific T Cell Clones For the functional analysis of T cell clones specific for nDer p2 and nDer p2-con j, T cell lines are initially derived from MNC of two atopic donors (G. E. and M. A.) affected by bronchial asthma and allergic rhinitis and sensitized to *Dermatophagoides pteronyssinus*, in the presence of nDer p2- or its respective conjugate nDer p2-conj. As control, from donor G. E. T cell lines specific for nDer p2 in the presence of R-848 (which has been already described as able to induce a redirection of $T_H2$ cells towards a $T_H1/T_H0$ oriented phenotype) have been also obtained. 28 allergen-specific T cell clones are obtained from T cell lines specific for nDer p2 from donor G. E. and 37 from donor M. A. whereas 28 clones are obtained from T cell lines derived in the presence of nDer p2-conj from both donors. Twelve clones specific for nDer p2 were also obtained from donor G. E. starting from T cell lines cultured in the presence of nDer p2 and soluble R-848. The clonal efficiency in the different culture conditions is shown in the table below:

| Donor | Clonal Efficiency (%) | | |
|---|---|---|---|
| | nDer p2 | nDer p2 + R-848 | nDer p2-conj |
| G.E. | 24 | 12 | 21 |
| M.A. | 30 | Nd | 37 |

The allergen-specific clones obtained in the different experimental conditions have been then assessed for their ability to produce IL-4 (µg/ml) and IFN-gamma (pg/ml) in the culture supernatants after polyclonal stimulation with PMA and anti-CD3 monoclonal antibody.

Figure 7:
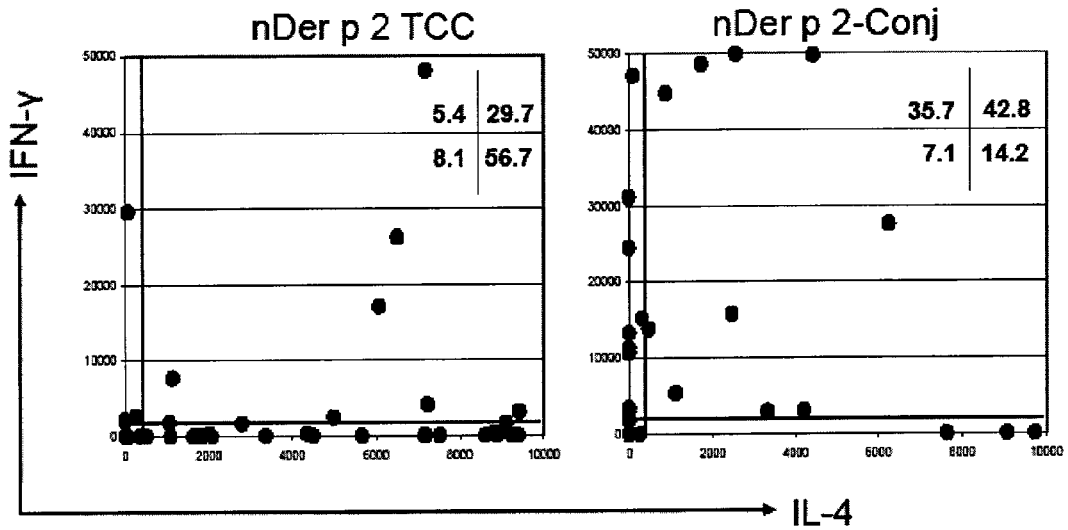
FIG. 7 shows IFN-gamma (y-axis) and IL-4 (x-axis) production (expressed as pg/ml) from T cell clones specific for the purified allergen nDer p2 (30 clones) or its respective conjugate nDer p2-conj (Conj-5) (37 clones) after polyclonal stimulation with PMA and anti-CD3 as specified in the Example 5 (step b). The amounts of IFN-gamma and IL-4 produced by feeder cells alone are shown as red dotted lines. In the square the percentages of clones able to produce IFN-gamma alone ($T_H1$ cells, up left), IL-4 alone ($T_H2$ cells, low right), both cytokines ($T_H0$ cells, up right) or no cytokine (low left) are indicated. The represented clones have been derived from the donor M. A.

The results obtained in step (a) have been confirmed at clonal level [Example 5 (step b)] as shown in the FIG. 7. In donor M. A. virtually all the clones obtained from the nDer p2-specific T cell lines produced IL-4 (x-axis, pg/ml) (23 clones) alone (21 clones, 56.7%) or together with IFN-gamma (y-axis, pg/ml) (11 clones, 29.7%), thus showing a clear-cut $T_H2/T_H0$ phenotype. On the other hand, when the conjugate nDer p2-conj is added at the beginning of the culture, only 4 clones are able to produce IL-4 (14.2%) whereas 10 clones (35.7%) exhibit a $T_H1$ phenotype and twelve a $T_H0$ phenotype (42.8%). In donor G. E. the unconjugated allergen nDer p2 expand 21 allergen-specific clones able to produce IL-4 (75%) alone or together with IFN-gamma, whereas the conjugated nDer p2 expand 7 clones (23%) producing IFN-gamma alone (thus exhibiting a clear-cut $T_H1$ profile) and 11 (48%) also producing IL-4 but none able to produce IL-4 alone.

In the FIG. 7 the data obtained from donor M. A. are shown. The square shows the percentages of clones producing the indicated cytokines (nDer p2 37 clones, nDer p2-conj 28 clones) are shown.

Step (c) Procedure to Monitor the Phenotype of
Allergen-Specific CRTH2 Cells

Mononuclear cells from peripheral blood (MNC) are isolated by density gradient (Ficoll-Hypaque) using buffy coats from *Dermatophagoides pteronyssinus*-sensitized donors (Servizio Immunotrasfusionale e terapie cellulari, Azienda Ospedaliero Universitaria Pediatrica A. Meyer, Firenze). $500 \times 10^6$ MNC are separated by the addition of 500 µl anti-CRTH2 monoclonal antibody for 20 min at room temperature, then extensively washed and incubated again with a secondary polyclonal antibody bound to iron microbeads and finally positively selected on a magnetic column (LS column). $10 \times 10^6$ cells are recovered by positive selection, extensively washed with sterile calcium and magnesium-free PBS buffer and cultured at the concentration $1 \times 10^6$/ml/well in complete medium plus 5% human AB serum in 24-flat bottomed plates. As stimulants, unconjugated allergens (DP or nDer p2) or conjugates (DP-conj or nDer p2-conj) (all at 10 µg/ml) have been used. Cultures have been incubated for 6 days at 37° C. in 5% $CO_2$ humidified atmosphere and further expanded with rIL-2 25 UI/ml until 14 days when T cell blasts are collected, extensively washed, counted, adjusted at $1 \times 10^6$/ml concentration and polyclonally stimulated with PMA and ionomicin as already described to assess the intracellular production of IL-4 and IFN-gamma.

The study of CRTH2 cells [Example 5 (step c)] has definitely confirmed the modulatory activity of conjugated compounds. In fact, CRTH2 cells, when in vitro stimulated with the unconjugated allergen, express IL-4, whereas, when cultured with conjugated allergen, the expression of IL-4 is dramatically reduced together with increased ability to produce IFN-gamma alone ($T_H1$ cells) or together with IL-4 ($T_H0$ cells).

The results obtained are shown in the following table:

| Donor | Allergen | % of cells ex pressing the indicated cytokine | | |
|---|---|---|---|---|
| | | IL-4+ | IL-4+ IFN-gamma+ | IFN-gamma+ |
| #1 | Dp extract | 85.5 | 1.5 | 0.3 |
| | DP-conj | 72.5 | 12.5 | 1.7 |
| #2 | Dp extract | 87.6 | 1.1 | 0.6 |
| | DP-conj | 49.2 | 6.0 | 19.8 |
| #3 | nDer p2 | 47.6 | 1.3 | 5.8 |
| | nDer p2-conj | 33.1 | 5.5 | 18.5 |
| #4 | nDer p2 | 78.2 | 2.3 | 2.0 |
| | nDer p2-conj | 52.1 | 19.3 | 17.8 |

Figure 8:
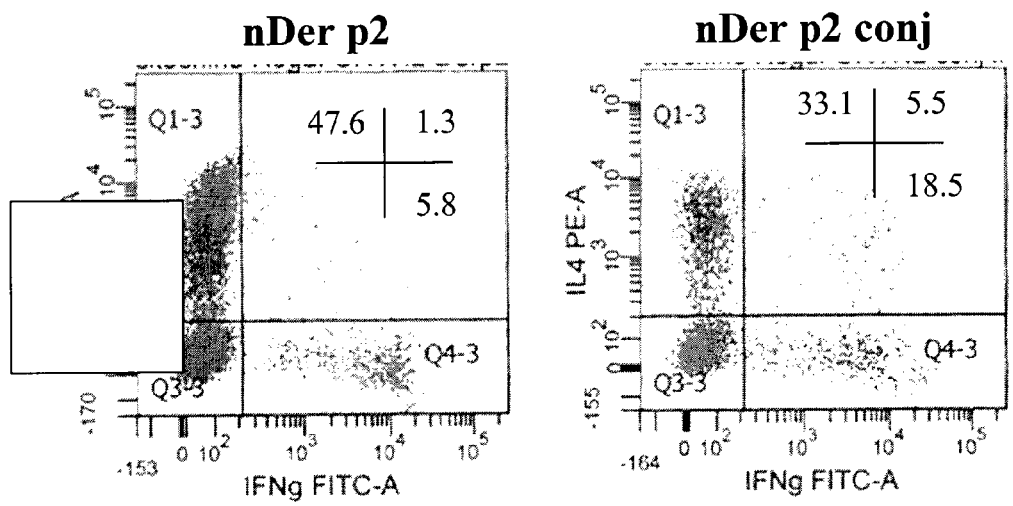
FIG. 8 shows the expression of IL-4 (y-axis) and IFN-gamma (x-axis) from of T-cell lines specific for the purified allergen nDer p2 or its respective conjugate nDer p2-conj (Conj-5) obtained from CRTH2+ cells after stimulation with PMA and ionomicin by cytofluorimetric analysis as specified in the Example 5 (step c). In the square the percentages of clones able to produce IL-4 alone ($T_H2$ cells, up left), IFN-gamma alone ($T_H1$ cells, low right), both cytokines ($T_H0$ cells, up right) or no cytokine (low left) are indicated. A representative experiment is shown (donor #3).

In the FIG. 8 a representative case is shown.

In the T cell lines no significant production of IL-17 that is claimed to be related to the induction of autoimmune diseases following TLR triggering, has been observed whereas a statistically significant reduction in the production of other $T_H2$-related cytokines (IL-5, IL-13) is found (data not shown).

Step (d) Procedure to Monitor the Functional
Phenotype of Allergen-Specific Cells with Different
Ratios between Allergen and Modified Adenine T cell lines derived from two atopic donors sensitized to *Dermatophagoides pteronyssinus* have been obtained as already described in step (a) by the use of unconjugated nDer p2 and three different preparations of conjugated allergens (as indicated in table Example 2: nDer p2-conj2, nDer p2-conj5, nDer p2-conj6), the three conjugated allergens being obtained by the same procedure of conjugation as described in Example 2 but mixing fixed amounts of nDer p2 protein with different amounts of the active ester SA-26E (step b) (Conj-2>Conj-5) or mixing fixed amounts of nDer p2 protein and similar amounts of the active ester SA-26E in different times (Conj-5 and Conj-6).

The conjugated compounds obtained with different ratios between the allergenic protein and the modified adenine (see table Example 2) tested in two atopic donors [Example 5/step d)] are able to significantly reduce the expression of IL-4, IL-5 and IL-13 (together with the $T_H2$-related transcription factor GATA-3) and to increase the expression of IFN-gamma in comparison with the T cell line obtained by the use of the unconjugated nDer p2 (data not shown). The $T_H1$-indicing effect is higher when the conjugated product nDer p2-conj 5 (lower amount of conjugated adenine) is used in comparison with Conj-2 (higher amount of conjugated adenine) whereas similar effects as obtained when Conj-5 or Conj-6 are used. This indicates that a) the amount of active ester conjugated to the allergenic molecule is critical for the functional modulation of the allergen-specific cells; b) the amount of active ester can be easily modified in order to obtain effects of different entity; c) the better modulatory effects are obtained with lower amounts of active ester conjugated to the antigenic protein.

As expected, R-848 is indeed able to decrease the percentage of the cells able to produce IL-4 together with a parallel increase of IFN-gamma production. Conjugated compounds produced in identical experimental conditions (i.e. nDer p2-conj 5 and nDer p2-conj 6) but at different times exert analogous effects thus indicating the optimal repeatability of the experiments.

| Experimental condition | % of cells expressing the indicated cytokine | |
|---|---|---|
|  | IL-4+ | IFN-gamma+ |
| nDer p2 | 55.5 | 5 |
| nDer p2 + R848 | 3.7 | 17.3 |
| nDer-conj2 | 32.3 | 18.9 |
| nDer-conj5 | 3.8 | 12.5 |
| nDer-conj6 | 4 | 14 |

Step (e) Procedure to Monitor the Modulatory Activity of Innate Cells on the Phenotype of Allergen-Specific T Cells To demonstrate that the cytokines produced by the antigen presenting cells after the stimulation with the conjugated product are indeed responsible of the functional modification of the phenotype of allergen-specific T lymphocytes, allergen-specific T cell lines have been obtained from two atopic donors by the use of DP and DP-conj in the absence or presence of neutralizing anti-IL12 (R&D System), anti-IL-29 (R&D System), anti-IFN-alfa and anti-IFN-alfaR (both from PBL, Piscataway, N.J., USA) monoclonal antibodies, each at 5 µg/ml, using the same procedure described in step (a). As negative control, mouse IgG were used.

The redirection effect exerted by conjugated products on T cells are dependent of their ability to stimulate the production of modulatory cytokines from cells of the innate immunity. Actually, in the two donors of Example 5 (step e), the addition of anti-IL-12 or anti-IFN-alfa antibodies to the cells cultured in the presence of DP-conj is able to restore the production of IL-4 (and to reduce the production of IFN-gamma) induced by the conjugated compound, whereas the neutralization of IL-29 does not exert any inhibitory effect. The mixture of anti-IL-12 and anti-IFN is indeed able to completely inhibit the modulatory activity of the conjugated allergen thus suggesting that these two cytokines are both involved in the $T_H1$ switching effect whereas the activity of IL-29 is not significant.

The results of the experiments are shown in the table reported below:

| Allergen | Antibody | % of the cells producing the following cytokines | | |
|---|---|---|---|---|
|  |  | IL-4+ | IL-4+ IFN-γ+ | IFN-γ+ |
| Donor #1 | | | | |
| DP |  | 28.6 | 15.6 | 14.1 |
| DP-conj |  | 1.9 | 4.3 | 40.6 |
| DP-conj | Mouse IgG | 1.9 | 1.8 | 27.7 |
| DP-conj | Anti-IL-29 | 1.5 | 1.7 | 41.0 |
| DP-conj | Anti-IL-12 + anti-IFN-α | 39.9 | 5.2 | 17.7 |
| DP-conj | Anti-IL-12 + anti-IFNα + anti-IL-29 | 45.9 | 6.9 | 16.0 |
| Donor #2 | | | | |
| DP |  | 39.3 | 7.3 | 17.5 |
| DP-conj |  | 6.5 | 12.5 | 63.9 |
| DP-conj | Mouse IgG | 6.1 | 5.7 | 57.3 |
| DP-conj | Anti-IL-29 | nd | nd | nd |
| DP-conj | Anti-IL-12 | 20.3 | 7.6 | 33.4 |
| DP-conj | Anti-IFN-α | 16.1 | 3.3 | 50.2 |
| DP-conj | Anti-IL-12 + anti-IFN-α + anti-IL-29 | 48.5 | 1.9 | 10.7 |

Step (f) Procedure to Monitor Allergen-Specific Recognition

In order to evaluate whether the allergenic conjugate is correctly recognized by *Dermatophagoides*-specific T lymphocytes, T cell lines are induced from peripheral blood mononuclear cells of three atopic donors by the use of the procedure already described in step (a) with unconjugated DP allergen. At the end of the 14 d culture period, T cell blasts are collected, washed and counted and finally cultured at the concentration $1 \times 10^6$/ml together with $1 \times 10^6$ autologous irradiated (9000 R) mononuclear cells as APCs in the presence of DP or DP-conj (10 µg/ml). After three days, tritiated thymidine is added for further 16 hrs. The incorporated radioactivity in the single cultures, measured as counts per minute (cpm) and directly proportional to the amount of tritiated thymidine incorporated in the cellular DNA, is evaluated after cell transfer on cellulose filters by the use of a cell Harvester (Tomtec, Turku) and read in a beta-counter. The cell proliferation is expressed as Stimulation Index (I) which is calculated as follows:

Mean cpms in stimulated cultures×100

Mean cpms in Unstimulated Cultures

Figure 9:
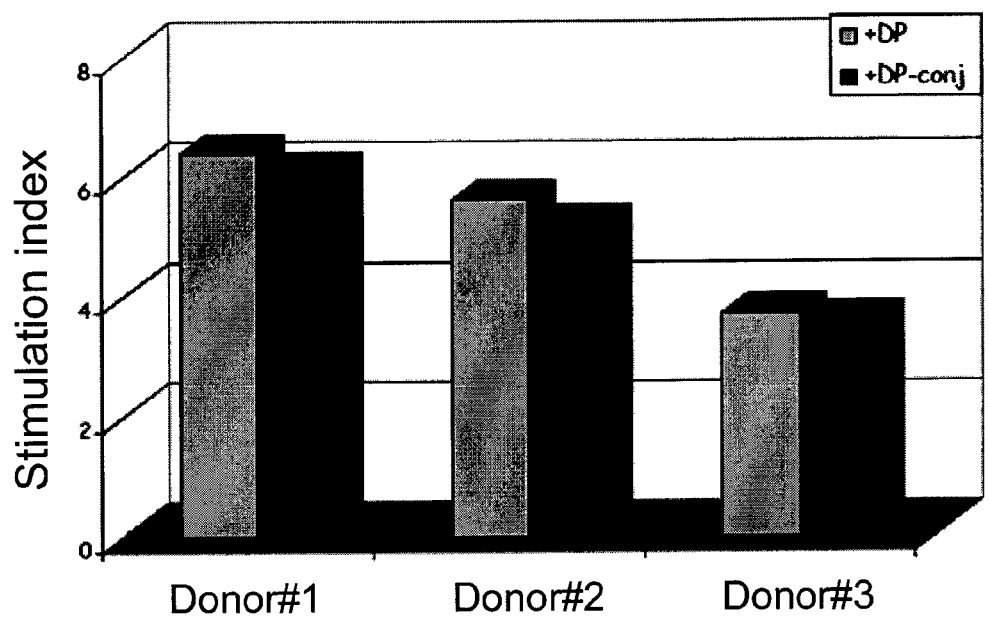
FIG. 9 shows the proliferation of T cell blasts from T cell lines specific for the DP allergenic extract from three different donors towards the native DP or its respective conjugate DP-conj in the presence of autologous irradiated mononuclear cells used as APC as specified in the Example 5 (step f). The proliferation is evaluated as stimulation index in comparison with the negative control (T cell blasts cultured in the presence of autologous presenting cells alone in the absence of the allergen).

The modulatory effect is not correlated to the loss of recognition of the conjugated allergen by T cells, as DP-specific T cell lines [Example 5 (step f)] equally proliferate in response to DP or conjugated DP as shown in FIG. 9. This indicates that the coupling procedure of the allergen does not modify the allergenic structure which is correctly recognized by specific T cells.

Example 6

Evaluation of the Effects on Other Cell Types

Step (a) Procedure to Monitor the Activation of Basophils

100 µl whole blood from four allergic patients sensitized to *Dermatophagoides pteronyssinus* were incubated together with 20 μl stimulation buffer (negative control) provided by the manufacturer (Becton Dickinson) or 20 μl serial dilutions of DP or nDer p2 or their respective conjugates DP-conj or nDer p2-conj (0.5-0.05-0.005 μg/ml) or 20 μl fMLP or 20 μg anti-IgE monoclonal antibody as positive control for 15 min at 37° C. in water. At the end of the incubation, the samples are rapidly put in ice for 5 min in order to arrest basophil degranulation and coloured by the addition of 20 μl mixture of three different monoclonal antibodies (FITC anti-CD63, PE anti-CD123 and PerCP anti-HLA-DR) for 20 min in ice. The lysis and fixation of the cells is obtained by the addition of 2 ml of a pre-warmed solution for 10 min at room temperature to single tubes which are finally centrifuged, washed and analysed at the cytofluorimeter acquiring at least 500 CD123+ cells for each sample.

The circulating basophils (CD123+ HLA-DR-) obtained as specified [Example 6 (step a)] easily increase the expression of the CD63 molecule when placed in the presence of anti-IgE as shown in the example (mean of the expression 41.3±6.5%) as well as when fMLP (data not shown) or unconjugated allergens at serial concentrations are added. On the contrary, the conjugated DP looses the ability to activated FCεRI+ cells in a dose-dependent manner.

The results obtained by the use of the DP and DP-conj allergens are reported in the following table:

| Allergen | % of CD63+ cells (mean ± SE) | | |
|---|---|---|---|
| | 0.5 μg/ml | 0.05 μg/ml | 0.005 μg/ml |
| DP | 62.3 ± 8.5 | 47.3 ± 10.6 | 15.0 ± 1.9 |
| DP-conj | 56.1 ± 11.1 | 24.8 ± 11.2* | 4.0 ± 1.5** |

*p < 0.0.5;
**p < 0.005

Step (b) Procedure to Monitor B Cell Activation

Circulating mononuclear cells (MNC) are isolated by Ficoll-Hypaque density gradient from buffy coats of healthy donors (Servizio Immunotrasfusionale e terapie cellulari, Azienda Ospedaliero Universitaria Pediatrica A. Meyer, Firenze). 200×10$^6$ MNC are then separated using the commercial CD19 isolation kit (Miltenyi) by the addition of 400 μl iron microbead-bound anti-CD19 monoclonal antibody followed by magnetic separation on LS column. 20×10$^6$ B cells are isolated by positive selection and are extensively washed by the use of calcium- and magnesium-free PBS and cultured in triplicates at the concentration of 1×10$^6$/ml/well in complete medium plus 10% foetal calf serum in 96-U plates. As stimulants, the following compounds are used: unconjugated allergens (DP or nDer p2) (10 μg/ml), their respective conjugates DP-conj or nDer p2-conj (10 μg/ml), R-848 (2 μg/ml) and CpG-ODN 2006 (10 μg/ml). Plates are incubated in humidified atmosphere at 37° C. for 72 hrs and at the end 0.5 μCi tritiated thymidine is added to each well for further 16 hrs. The incorporated radioactivity is measured as already described in step (f) of Example 4.

Soluble TLR-ligands (R-848 and CpG) are able to induce high levels of incorporation of radioactive thymidine in purified B cells [Example 6 (step b)] as expressed by stimulation indexes whereas the conjugated allergens exhibit a low or absent ability to induce proliferation thus showing a better safety profile. As expected, the unconjugated allergens are unable to determine any proliferative response in B lymphocytes.

The results regarding the experiments with the purified allergen nDer p2 and its respective conjugate are reported in the table below:

| Stimulant | Concentration | Stimulation index (mean ± SE) |
|---|---|---|
| CpG | 10 μg/ml | 90.3 ± 7.5 |
| R-848 | 2 μg/ml | 71.7 ± 7.5 |
| nDer p2 | 10 μg/ml | 1.7 ± 0.1 |
| | 2.5 μg/ml | 1.7 ± 0.2 |
| | 0.5 μg/ml | 1.6 ± 0.4 |
| nDer p2-conj | 10 μg/ml | 3.8 ± 0.4 |
| | 2.5 μg/ml | 1.7 ± 0.2 |
| | 0.5 μg/ml | 1.6 ± 0.0 |

Example 7
Evaluation of the In Vivo Effects of Conjugates in an Experimental Model of Murine Asthma

Step (a) Procedure to Measure the Bronchial Hyperreactivity

Ten BALB/C and ten C57BL/6 6-8 wk-old female mice (Charles River) have been intraperitoneally sensitized at day 0 and d 7 with 10 μg OVA (5 animals per strain) or OVA-conj (5 animals per strain) in the presence of alum. At d 14 and d 18 animals are stimulated intratracheally with 10 μg OVA and after 24 hrs unspecific bronchial hyperreactivity is measured administering first an aerosolized PBS solution to obtain the standard value and then an aerosolized solution containing increasing concentrations of methacolin for 3 min (6.25-12.5-25-50 mg/ml). The pletismograph in which the animal is inserted is able to monitor the values of airflow resistance.

Step (b) Procedure to Measure the Modification of Antibody Response

Serum levels of total and OVA-specific IgE have been determined at d 14 and d 18 (before the intratracheal allergic stimulation) in sensitized animals by the use of commercial kits.

Figure 10:
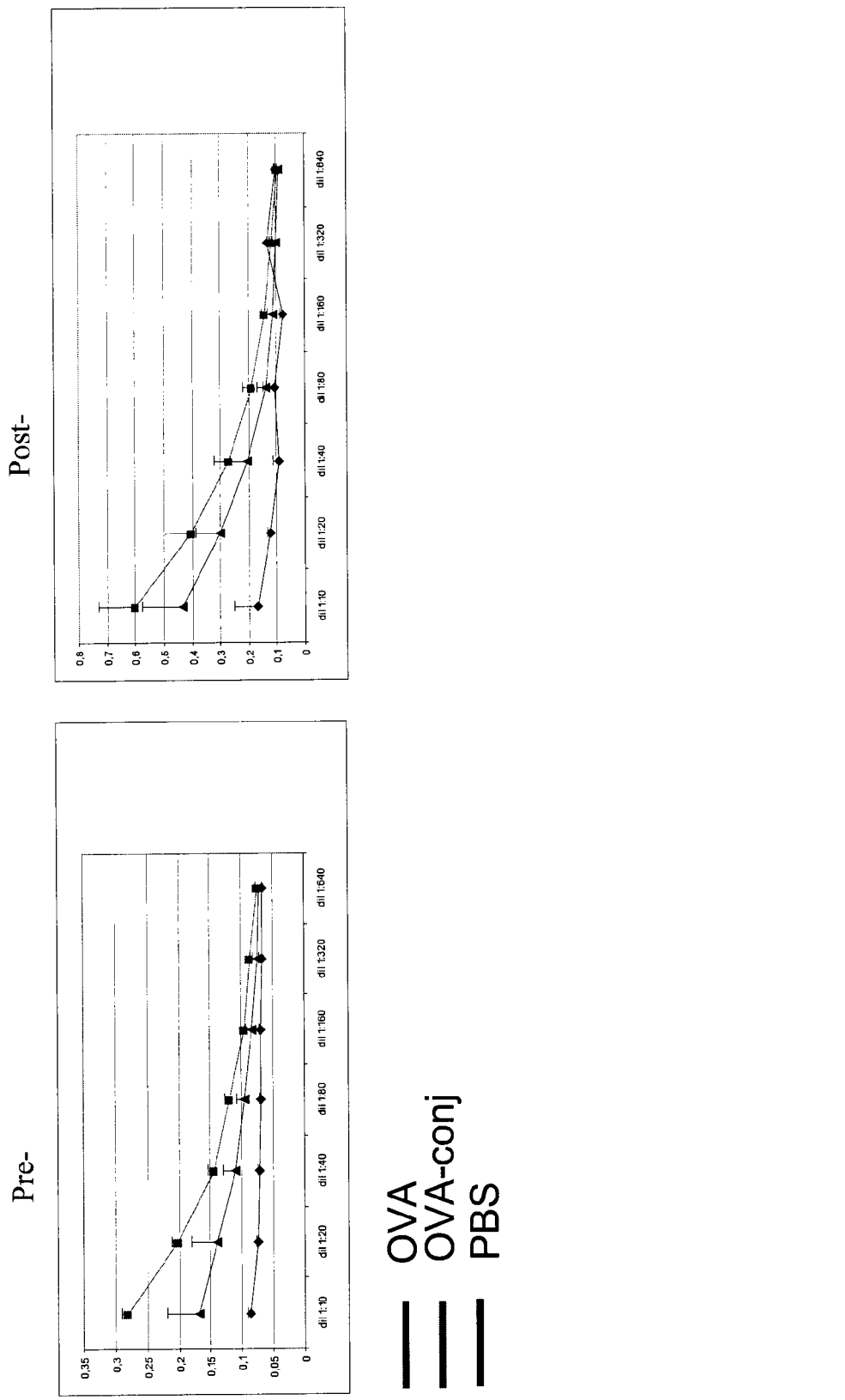
FIG. 10 shows the production of OVA-specific IgE from C57BL/6 mice (5 animals per group) which were sensitized for OVA (red squares) or its respective conjugate OVA-conj (red triangles) or PBS (control group) (blue diamond) before (left panel) or after (right panel) the intratracheal challenge with OVA as specified in the Example 7 (step b). The IgE values are evaluated by ELISA and are expressed as Optical Densities (y-axis) at various serum dilutions (x-axis, dilution ranging from 1:10 to 1:640).

The sensitization with OVA conjugated with modified adenine [OVA-conj] in the experimental animals following the procedure already described [Example 7 (step b)] induce reduced levels of IgE (both total IgE as shown in the table and OVA-specific IgE as shown in the following table and FIG. 10) in comparison with OVA-sensitized mice that exhibit, as expected, a significant activation of $T_H2$-related responses. In parallel, a significant increase in the levels of IgG2a class is found in the conjugated protein sensitized animals (data not shown).

| Sensitization | Total IgE (pg/ml) (mean ± SE) | |
|---|---|---|
| | d14 pre-challenge | d18 post-challenge |
| control | 190 ± 130 | 394 ± 50 |
| OVA | 966 ± 268 | 680 ± 234 |
| OVA-conj | 780 ± 64 | 618 ± 91 |

Figure 11:
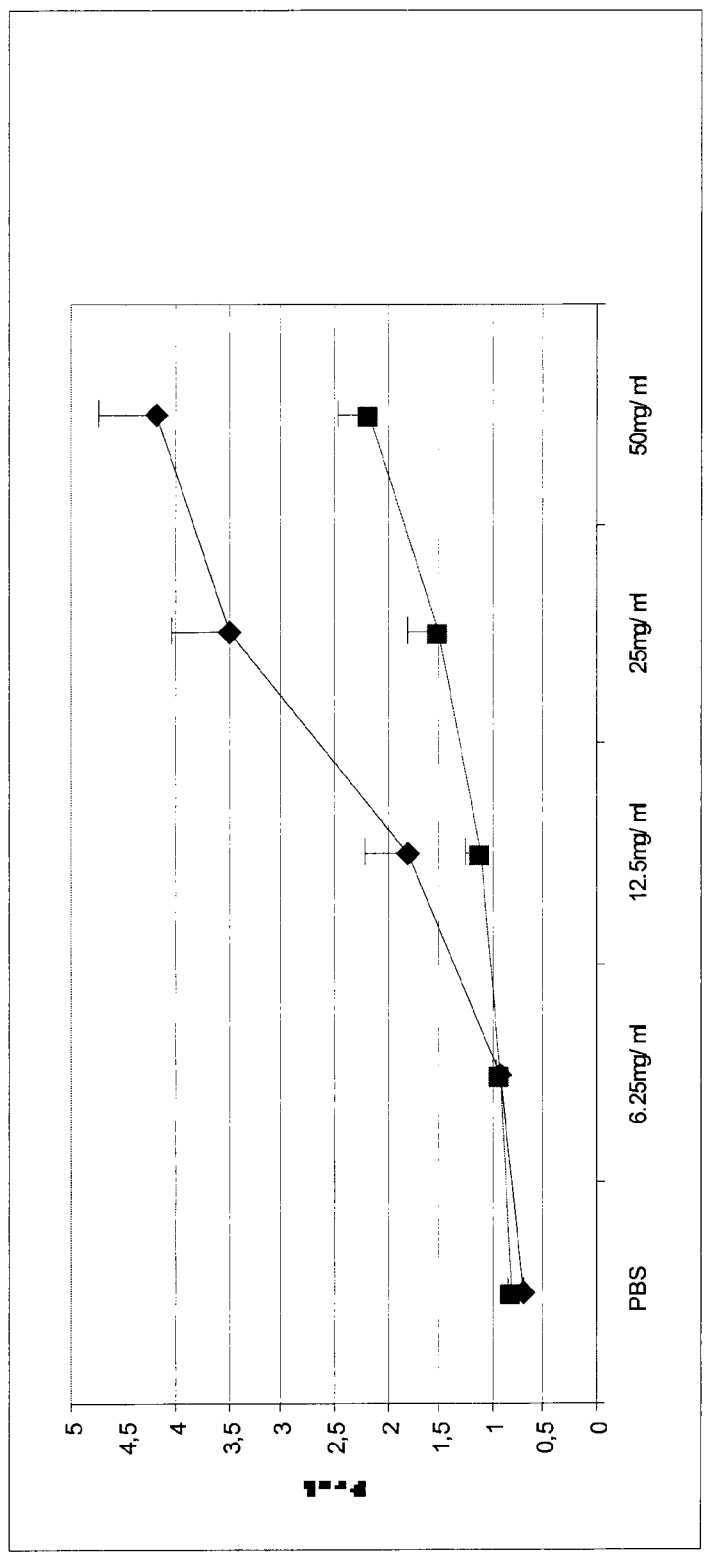
FIG. 11 shows the airway hyperreactivity of C57BL/6 mice sensitized with OVA (blue line) or its respective conjugate OVA-conj (red line) after inhalation of progressively increasing concentrations of methacolin (6.25-12.5-25 and 50 mg/ml) in comparison with the basal value evaluated by PBS inhalation as specified in Example 7 (step a).

Moreover, the group of animals sensitized by the use of the conjugated compound OVA-conj exhibit a significant decrease in the methacolin-induced bronchial hyperreactivity [Example 7 (step a)] in comparison with unconjugated OVA-sensitized mice, thus suggesting that the conjugation of OVA together with the modified adenine is indeed able to significantly reduce the bronchial hyperreactivity following the inhalation of allergenic proteins such as OVA (see FIG. 11). These data are well correlated with the reduction of the proportion of eosinophils in the bronchoalveolar lavage (data not shown).

The invention claimed is:

1. A stable conjugated compound of formula (II):

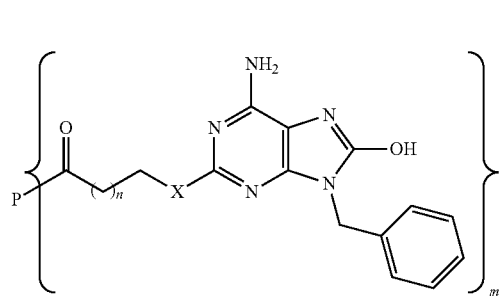

wherein X=S;

n is an number from 2-10;

P is a protein, having antigenic activity which is bound through at least one lysine residue to (II); and m is a number ranging from 1 to the number of available lysine residues on said P protein.

2. The compound according to claim 1 wherein P is selected from the group consisting of a bacterial antigen, an inhaled allergen and a food allergen.

3. A method for eliciting an antigen specific immune response against a protein P comprising administering to a subject suffering from an immunological disease caused by said protein a compound of claim 1, in an amount sufficient to elicit an antigen-specific immune response against protein P.

4. The method according to claim 3, wherein said immunological disease is an allergic disease to protein P.

5. A pharmaceutical composition comprising at least one compound of claim 1, and a pharmaceutically acceptable ingredient.

6. A process for the preparation of a compound of claim 1, said process comprising conjugating P with an acid of formula (V):

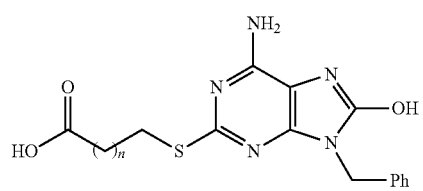

or a corresponding activated ester to form said compound.

7. The process according to claim 6 wherein (V) is an activated ester of formula (I):

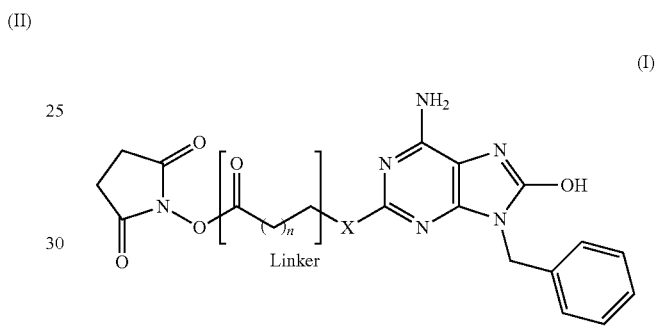

wherein X=S and n is a number between 2 and 10.

8. A process according to claim 6 wherein said compound of formula (V) or said corresponding activated ester is obtained from a compound of formula (III):

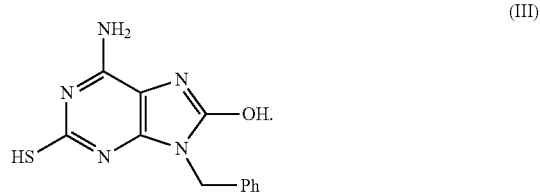 [SMILES: Nc1nc(S)nc2c1nc(O)n2Cc1ccccc1]

9. A compound of formula (I):

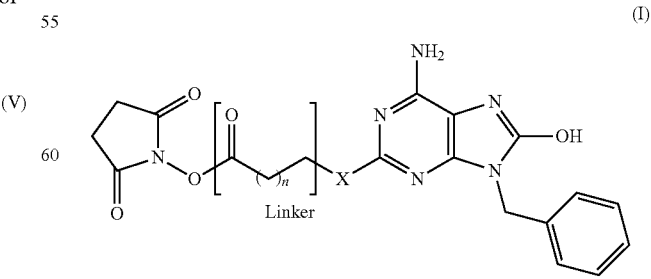

wherein X=S and n is a number from 2 and 10.

10. The conjugate according to claim 2 wherein P is selected from the group consisting of a house dust mite *Dermatophagoides pteronyssinus* (DP) antigen, Der p2 and Ovalbumin.

11. The compound of claim 1, wherein n is 2-4.
12. The compound of claim 1, wherein n is 2.
13. The compound of claim 12, wherein P is Der p2.
14. The compound of claim 13, wherein and m is 1.
15. The compound of claim 1, wherein m is 1.
16. The compound of claim 1, wherein P is Der p2.
17. The compound of claim 1, wherein m is 1 or 2.
18. The compound of claim 12, wherein m is 1 or 2.
19. The compound of claim 9, wherein n is 2-4.

* * * * *

SEQUENCE LISTING

```
<160> NUMBER OF SEQ ID NOS: 1

<210> SEQ ID NO 1
<211> LENGTH: 10
<212> TYPE: DNA
<213> ORGANISM: Dermatophagoides pteronyssinus
<220> FEATURE:
<221> NAME/KEY: source
<222> LOCATION: 1..10
<223> OTHER INFORMATION: /mol_type="DNA"
      /organism="Dermatophagoides pteronyssinus"

<400> SEQUENCE: 1
gggactttcc                                                          10
```